US010363192B2

(12) United States Patent
Casey

(10) Patent No.: US 10,363,192 B2
(45) Date of Patent: Jul. 30, 2019

(54) DEVICE AND METHOD FOR INSTILLING INTRINSIC MOTIVATION REGARDING EYE CONTACT IN CHILDREN AFFECTED BY EYE CONTACT DISORDERS

(71) Applicant: Matthew Casey, Woburn, MA (US)

(72) Inventor: Matthew Casey, Woburn, MA (US)

(73) Assignee: Matthew Casey, Woburn, MA (US)

( * ) Notice: Subject to any disclaimer, the term of this patent is extended or adjusted under 35 U.S.C. 154(b) by 26 days.

(21) Appl. No.: 15/184,003

(22) Filed: Jun. 16, 2016

(65) Prior Publication Data

US 2017/0360647 A1 Dec. 21, 2017

(51) Int. Cl.
*A61H 5/00* (2006.01)
*G06F 3/01* (2006.01)
*A61B 3/113* (2006.01)

(52) U.S. Cl.
CPC ............... *A61H 5/00* (2013.01); *A61B 3/113* (2013.01); *G06F 3/013* (2013.01); *A61H 2201/1207* (2013.01); *A61H 2201/1673* (2013.01); *A61H 2201/5007* (2013.01); *A61H 2201/5092* (2013.01)

(58) Field of Classification Search
CPC .......... A61H 5/00; A63H 3/001; A63H 3/003; A63H 3/40; G06N 3/008
See application file for complete search history.

(56) References Cited

U.S. PATENT DOCUMENTS

| | | | | |
|---|---|---|---|---|
| 8,715,033 B2 * | 5/2014 | Smoot | ..................... | A61F 2/141 446/131 |
| 2002/0198626 A1 * | 12/2002 | Imai | ...................... | G06N 3/008 700/245 |
| 2004/0249510 A1 * | 12/2004 | Hanson | .................. | G06N 3/008 700/245 |
| 2010/0041306 A1 * | 2/2010 | Yang | ........................ | A63H 3/40 446/343 |
| 2011/0066239 A1 * | 3/2011 | Smoot | ..................... | A61F 2/141 623/6.64 |
| 2013/0078600 A1 * | 3/2013 | Fischer | .................. | G09B 19/00 434/236 |
| 2013/0130587 A1 * | 5/2013 | Cohen | .................... | A63H 30/04 446/175 |
| 2015/0298315 A1 * | 10/2015 | Shick | ..................... | G06N 3/008 700/246 |
| 2017/0209796 A1 * | 7/2017 | Kim | ........................ | A63H 3/003 |

* cited by examiner

*Primary Examiner* — Kristen Matter

(57) ABSTRACT

This describes a treatment method for autism/ASD intended to encourage greater eye contact by affected children. The treatment method incorporates an artificial demonstration of the phenomenon of eye contact, and that method is described herein along with the principles of action of the treatment and the necessary procedure to perform it. Also described are two embodiments of the physical portion of the invention that can be used for the demonstration: first, an item in the form of a cuboid with animatronic eyes affixed to one side that most purely reflects the principles behind the treatment, and second, another in the form of a stuffed toy that is perhaps more practical.

11 Claims, 3 Drawing Sheets

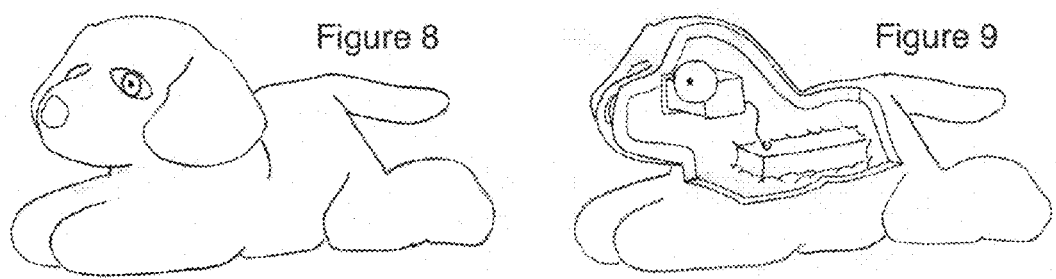
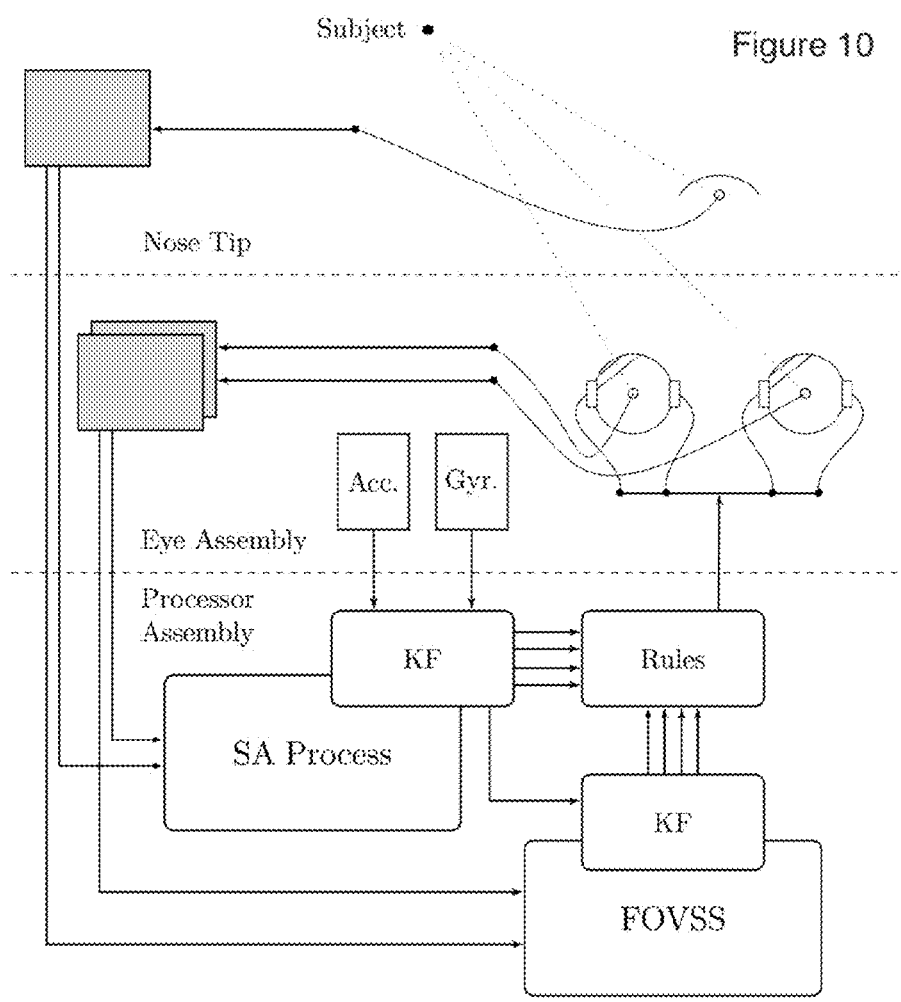

DEVICE AND METHOD FOR INSTILLING INTRINSIC MOTIVATION REGARDING EYE CONTACT IN CHILDREN AFFECTED BY EYE CONTACT DISORDERS

[Abstract] This describes a treatment method for autism/ASD intended to induce greater intrinsic motivation to make eye contact in affected children. The treatment method incorporates an artificial demonstration of the phenomenon of eye contact, and that method is described herein along with the principles of action of the treatment and the necessary procedure to perform it. Also described are two embodiments of a therapy tool that can be used to effect the demonstration: first, an item in the form of a cuboid with animatronic eyes affixed to one side, and second, another in the form of a stuffed dog.

FIELD OF THE INVENTION

The invention is in the field of medical devices and treatments. More specifically, it is a treatment that uses an accompanying device to improve eye-gaze behavior in individuals who have an aversion to eye contact due to neurodevelopmental disorders such as autism or other autism spectrum disorders (ASD). A novel tool for use in the therapy has characteristics such that it might be considered to be in the realms of consumer electronics, robotics, and education technology.

BACKGROUND AND RELATED ART

Eye contact is an important component of human-to-human communication, being used often by both children and adults to communicate with most others in their daily lives. Children who habitually fail to make eye contact often face challenges and difficulties in life that most people do not, and failing to make eye contact is a common sign of autism. In fact, according to AutismTreatmentCenter.org, eye contact (alongside speech) is one of the main development challenges faced by children with autism, and as such, it is not surprising that the topic has been addressed many times by numerous researchers. Here I quote a passage from a 2013 paper by Carbone et al in reference to prior research in the field in which the authors cite several other works:

"It has been suggested that eye contact, sometimes referred to as (eye) gaze behavior or eye-to-face gaze (Mirenda, Donnellan, & Yoder, 1983) serves an important social function for young children even before vocal responding begins to develop (Stern, 1985). In early development, eye contact serves to regulate face-to-face social interactions (Lee, Eskritt, Symons, & Muir, 1998; Leekam, Baron-Cohen, Perrett, Milders, & Brown, 1997) and contribute communicatively to social interactions (Tiegerman & Primavera, 1984). Later, eye contact responses coordinate the visual attention between another individual and an object of interest (Arnold, Semple, Beale, & Fletcher-Flinn, 2000) and have been found to be an influencing variable in language acquisition (Podrouzek & Furrow, 1988).

"Deficits in various nonverbal social-communicative behaviors, particularly in dyadic (i.e., eye-to-face) and triadic eye gaze (i.e., joint attention directed at a third party or object) are commonly identified as the earliest indicators and most noticeable deficits of developmental delays and of Autism Spectrum Disorder in particular (Baron-Cohen, Allen, & Gillberg, 1992; Mirenda et al., 1983; Wimpory, Hobson, Williams, & Nash, 2000; Woods & Wetherby, 2003). Because of the various social functions eye contact may serve, failure to emit this important behavior may have significant implications for children with autism. In addition, there are possible educational concerns associated with poor eye contact. Specifically, previous research has suggested that the diversity of prelinguistic pragmatic skills exhibited (e.g., eye contact, joint attention) is predictive of the rate of subsequent vocabulary acquisition (Kleinke, 1986) and it has also been suggested that poor eye contact may adversely affect the educational gains of children with autism due to the relationship between eye contact and attending to the teacher and instructional demands (Greer & Ross, 2007; Lovaas, 1977)."
(Carbone et al, 2013)

Autism spectrum disorders, including autism itself, are characterized by "(a) impaired social interactions and failure to develop social relationships, (b) impaired and disordered language and communication, and/or (c) occurrence of restricted and repetitive behaviors." Boys are affected 3 to 4 times more often than girls. The cause of ASD is considered unknown in 90 to 95 percent of cases (Boyd et al, 2010).

Ultimately, "there is no aetiology-based intervention for [ASD]" (Francis, 2005) and consistent with this, credible therapies tend to address the symptoms of the condition—behaviors—rather than any biological causes. Similarly, pharmacological treatments are available for "hyperactivity, impulsivity, inattention, aggression, irritability, anxiety, and withdrawal," but do not address any root cause of the condition. (Tchaconasa and Adesman, 2013) Special diets—casein-free, gluten-free, etc.—aimed at the problem, typically have no scientific basis. Early intervention—starting when the child is as young as possible—is generally considered important in obtaining a good prognosis.

There are numerous strategies that are used by psychiatrists, therapists, parents, teachers, professionals, and other caregivers in the treatment of autism. For the purposes of this discussion of prior art, I will with great generality classify these strategies as being largely of three types. First, there are those based heavily on the principles of Applied Behavior Analysis (ABA), principles that although they have been upheld by the medical community for decades, and have considerable research demonstrating their effectiveness statistically, are not without criticism. Second, there are many alternative therapies that often come to be favored by parents due to a somewhat softer approach to the condition. Some of these are without any scientific basis, and others simply lack hard supporting data, though more recently, some aspects of these child-directed and natural environment therapies have found better support from research. Third, there are strategies that combine aspects of each of the first two types, and such hybrid strategies are of growing popularity. After a brief overview of these strategies, I will indicate some of the ways that technology is being incorporated.

The most established treatments for autism and ASD in children—including and especially that targeting the important symptom/cause of problem eye-gaze behavior—typically involve aggressive therapy programs based on the psychological principles of Applied Behavior Analysis (ABA). ABA has been successfully used in the treatment of autism since the 1960s (Tchaconasa and Adesman, 2013), and uses positive and negative reinforcement in order to increase or decrease the prevalence of certain behaviors. It is often effected as Discrete Trial Training (DTT) whereby a simple antecedent stimulus is presented to the child, and the child's response to this stimulus can immediately be reinforced appropriately. In the context of treating eye-gaze behavior specifically, this extrinsic motivation might proceed with a caregiver providing an antecedent prompt to the child "look at me," and given a satisfactory response, the child would be given an edible reward (Brown and Bradley, 2014). Over time, after a number of discrete trials have begun to show progress towards the extinction of problem eye-gaze behavior, the use of edible rewards can be faded out. In this manner, ABA seeks to induce affected children to act in ways that in the future they will learn the benefits of.

ABA has gained great respect amongst practitioners due to peer-reviewed supporting research, including the work of Ivar Levaas, who in the late 1980s, began to produce some of most compelling empirical evidence demonstrating the effectiveness of ABA-DTT techniques in treating autism. Since then, many others have found the same, and today, ABA techniques are unique amongst treatment tactics in that they have found widespread acceptance and endorsement. For the purposes of treating autism, ABA has been formerly endorsed by many medical organizations including the American Academy of Neurology, the American Academy of Family Pediatrics, the American Academy of Pediatrics, the American Psychological Association, the American Speech-Language Hearing Association, the Society for Developmental and Behavioral Pediatrics, the Autism Society of America, the National Institute of Child Health & Human Development, and the National Institute of Mental Health; it is routinely touted by Autism Speaks, the largest autism-related nonprofit in the United States; and in 1999, it was endorsed by then United States Surgeon General Dr. David Satcher (appliedbehaviorcenter.com).

However, despite this obvious and thorough acceptance of ABA, some aspects of it have been criticized, including DTT in particular. Ultimately, ABA is something of a "carrot-and-stick" approach, and some critics have noted the potential superiority of intrinsic motivation. Some parents have expressed worry and/or dissatisfaction regarding the results as well, claiming that ABA can/could make their child act in ways that might be considered "robotic", exhibiting more desirable behaviors only because they were induced, and not as manifestations of the child's personality (iancommunity.org indicates Steege et al, 2007). In addition, while ABA techniques have never drawn the same level of ire as did the Behavior Modification techniques of the first half of the twentieth century, some formerly autistic children who have grown to become high-functioning adults have criticized aspects of ABA as unethical (Dawson, 2004). Part of this criticism is certainly due to the use of aversive consequences to discourage unwanted behaviors, techniques that-out of favor today-were notably used during Ivar Lovaas's seminal work on the subject. The following passage from a 1977 paper documents such an aversive technique:

"... the therapist said '[the child's name], you didn't look at me,' in a stern voice and then began functional movement training ... where the child was required to move his head in one of three directions-up, down, or straight and a verbal instruction was given for each position (e.g., 'head up'). The child had 1 sec in which to respond to the instruction, after which the therapist began guiding his head manually in the desired direction. The therapist stood behind the child, who remained seated throughout the functional movement training period. If the child began the desired movement at any time during the guidance, the guidance was eliminated and the therapist merely shadowed the child's head with her hands. However, she reapplied the guidance whenever the desired movement ceased. The child was required to sustain each posture for 15 sec. The order of the instructions was random so that the child would attend to the verbal instruction, rather than learning a particular sequence. Approximately 20 sec after the functional movement training period had ended, a new eye-contact trial was begun." (Foxx, 1977)

Ultimately, some researchers continue to note that in severe cases the use of aversive consequences may yield superior results than the use of positive reinforcement alone (Foxx, 2005). However, the diagnostic criteria for autism/ASD are, today, broader than they used to be, and the recent explosion in autism and ASD cases has resulted in many children being diagnosed with ASD who in previous generations would have had their conditions remain unrecognized (Gernsbacher, Dawson, and Goldsmith, 2005). For these less severe cases—perhaps the bulk of the cases today—strict implementations of ABA complete with aversives may be less appropriate.

The archetypal alternative to the strict application of ABA-DTT, might be called child-driven/directed or naturalistic. If ABA-DTT concerns a series of short iterations, each initiated by the therapist, each with a defined and measurable outcome, then a child-directed or naturalistic scheme focused around play is the opposite. Such a strategy is less rigidly defined and seeks to follow the child according to his/her interests, legitimizing those interests, and hopefully allowing for a bond to form between caregiver and subject. In the context of eye-contact, one may note the following suggestions as provided to a parent by the director of a therapy center that promotes a child-directed program:

"Position yourself at or below his eye level consistently. It's less eye strain and easier [for him] to look at you this way. When you give him an object, hold it to your eyes, so that he must reach out and grab it. You are right there, behind the object! Whenever [he] does look at you, celebrate him for it! Tell him how much you appreciate him looking. He may not know how special it is to you."—Bryn Hogan, Director, the Son-Rise Program (AutismTreatmentCenter.org)

In contrast to ABA, in which the therapist virtually—or even literally—might instruct/order/induce a child to notice, do, or say something, it seems that practitioners of a child-directed strategy prefer to actively compete for the child's attention. This is clearly a softer, gentler, more friendly approach.

Research regarding child-directed strategies is mixed, due perhaps to the significant variation between strategies. While a few child-directed programs aimed at parents tout miraculous results, often the research supporting such programs is simply anecdotal, with strict control groups typically absent, which leaves such programs unendorsed relative to ABA.

On the other hand, some credible research, as mentioned above, backs the use of some of the characteristic alternative techniques of child-directed/naturalistic strategies. For example, imitating an affected child's behavior-what might be considered a child-directed technique by definition—was shown as early as 1984, to, in some instances, result in greater eye contact (Tiegerman and Primavera, 1984). Other studies have also found similar results: for example, one observed that children responded favorably to a protocol that included contingent imitation on the part of the practitioner, and that in response, the child subjects demonstrated increased "use of eye gaze and [reciprocated] imitation [on the part of the child] of familiar actions that generalized to novel con-texts" (Hwang and Hughes, 2000, as cited by Ingersoll, 2008). Ultimately, these and other positive findings have likely influenced specific aspects of some treatment programs directly. Such would certainly seem to be the case for one strategy known as Reciprocal Imitation Training (RIT)—a strategy that notably contains ABA aspects, but also the very natural, child-driven technique of imitation. A general outline of the teaching components for RIT indicates specifically that in order for a caregiver to increase the level of eye contact on the part of a child that the caregiver might "imitate[s] the child's actions with toys, gestures/body movements, and vocalizations at the same time as the child." (Ingersoll, 2008)

Most recently, the trend has been toward programs that include aspects of ABA while also focusing more on the relationship between caregiver and subject, and expectedly, such finds more common support between professionals and parents who are both active in the treatment process. Examples include the Children's Toddler School, Project DATA for Toddlers, the Early Start Denver Model, the Early Social Interaction Project, and the Walden Toddler Program (Boyd et al, 2010). One resource notes that "sensory social routines such as peek-a-boo and 'I'm gonna get you,' provide opportunities for eye contact, child initiations to continue the activity, reciprocity, anticipation, joint attention and sensory regulation" (JustKidsSchool.com). Some have applied the moniker Natural Environment Teaching (NET), yet indicated treatment techniques such as the following:

> "A learner and a therapist are playing together, with the therapist tickling the learner (and tickling is preferred by the learner). The therapist then pauses tickling and looks expectantly at the learner with an anticipatory expression and hands raised in the air. After several seconds, the learner looks in the direction of the therapist, who immediately resumes the tickling activity, and praises the learner as soon as he makes eye contact." (Granpeesheh et al, 2014)

While the above seems far more natural than any procedure that might involve the use of edible rewards or functional movement training as described in Foxx's 1977 paper, the above suggested technique also clearly follows ABA's antecedent-response-consequence framework. Despite this, proponents of NET, at times, deride DTT: "while [DTT's] approach to increasing eye contact may have its benefits, it can often lead to individuals only making eye contact when instructed to do so or using patterns of eye contact that appear unnatural." (Granpeesheh et al, 2014) Truly, such would seem less likely with NET.

Turning now to the topic of applied technology, numerous technology products have been found helpful in both therapy as well as the education of children with autism. For example, teenagers with autism have been found to derive significant benefits from the use of Personal Digital Assistants (Gentry et al, 2010). Certain types of software that has been found to make subjects more engaged and less resistant to the learning process (Williams et al, 2002) as well as more attentive, more motivated, and ultimately apt to greater achievement (Moore and Calvert, 2000). Technology in the realm of Augmentative and Alternative Communication, especially Picture Exchange Communication Systems, has been very successful in both improving speech and facilitating alternative ways to communicate (Preston and Carter, 2009). Tablet computers have been found to be particularly useful in this context.

Very few software applications seem to have addressed the problem of eye contact specifically. A collaboration between Samsung and Autism Speaks has yielded the Look At Me product, a smartphone app that seems to aim at encouraging individuals to focus on eye contact as they take photos of other people. In addition, Goatella's Eye Contact Trainer app as well as the tablet apps of the Look In My Eyes series from FizzBrain LLC have a very simple, common game format aimed at the problem. Autism Speaks indicates the research supporting the use of the Look In My Eyes series as being "anecdotal" (autismspeaks.org); however, there may be some rightful skepticism about whether time spent with such tablet apps would truly increase the amount of attention that would later be paid to caregivers and people in general.

A number of robotic toys intended to help kids affected with autism have also been developed, and these developments are closely associated with the new and growing field of Socially Assistive Robotics (SAR). A 2012 review (Scassellati, Admoni, and Matarić, 2012) documented research regarding roughly a dozen robots of varying complexity—most having at least some anthropomorphic features—that might be used in the context of autism therapy. Most of the examples came from academic groups affiliated with universities such as the University of Southern California, the University of Hertfordshire, the University of Sherbrooke, University of Pisa, and Miyagi University. Very few of the robots discussed in this 2012 review were commercially available—perhaps limited to only two: each of "Pleo," a robotic dinosaur, and Sony's "Aibo," a robotic dog—and neither of these were specifically intended for therapeutic use, being preferentially aimed at a broader toy market.

> "The main intended role of a SAR system in autism therapy is to allow or encourage children to develop and employ social skills. To this end, robots can be designed to take part in numerous different interaction goals, such as capturing and maintaining attention, evoking joint attention, eliciting imitation, and mediating turn-taking." (Scassellati, Admoni, and Matarić, 2012)

Researchers typically give affected children the opportunity to interact with a robot in the presence of a therapist or in the presence of other children, usually over the course of several dedicated sessions during which the robot's ability to elicit effects can be assessed. The length of such sessions varies, depending most often on the attention span of the children (Cabibihan et al, 2013). Research has typically shown that—at least during the session—the robots have the distinct ability to improve socialization, not simply in relation to the robot, but in relation to other people who are present during the session.

> "In many studies, children with ASD interacting with robots show spontaneous joint attention behavior—for example, looking at an adult and back to the robot or pointing to the robot and looking at an adult or another child, with the intention of sharing some feature with that person. Children with autism show this behavior de-spite previously displayed tendencies to avoid eye contact or engagement with unknown adults." (Scassellati, Admoni, and Matarić, 2012)

This response on the part of affected children seems to mirror the response that would be seen in any person/group who/that might be confronted with something extremely new and different-amazement, the seeking of a sort of confirmation that their eyes are not deceiving them, and perhaps a general revelry in the experience. (For example, consider a group of people all absorbed in their own activities, work or otherwise. If a UFO were to suddenly land near them, it would draw all of their attention away from those individual activities, and those people would all proceed to socialize over their own amazement in the arrival of the UFO.)

What is more, it has been implied that such robots have some distinct advantages even in relation to the capability of human caregivers to elicit certain responses, the robots exploiting a distinct tendency of affected children to show an affinity for and more easily interact with things that are somewhat less than human.

"Some of these behaviors observed during interactions involving children with autism and robots can be attributed to the fact that robots provide novel sensory stimuli, but some-such as turn-taking with another child, manifestations of empathy, or initiation of physical contact with the experimenter-suggest that robots occupy a special niche between inanimate toys (which do not elicit novel social behaviors) and animate social beings (which can be a source of confusion and distress to children with autism). The goal of researchers investigating SAR for autism treatment is to develop robots that elicit these positive and productive interactions." (Scassellati, Admoni, and Matarić, 2012)

Since the 2012 review, two commercially available examples have moved to the forefront. One is Aldebaran Robotics's "NAO", a robot that was initially introduced in 2007 August for the purpose of teaching older—and for the most part, neurotypical—children about technology and robotics. Similar to Pleo and Sony's Aibo, units of NAO have—for general, not-necessarily autism-related use—been produced in the thousands, and since 2012, NAO has, given its widespread availability, been harnessed by numerous universities as an object for autism related studies. Research results seem to be mixed, with some reporting of increased joint attention and positive effects on eye gaze, and others of less impact on joint attention and eye gaze effects that only occur relative to the robot, not to humans present at the time or afterward (Tapus et al, 2012).

The second recent commercial robot of note—introduced in 2015—is that of RoboKind's "Milo" which, unlike other commercial examples, is specifically intended for autism treatment. Milo is related to a prior product, "Zeno", that was intended for use in robotics research and was in development since at least the mid 2000s. Peer-reviewed research on the effectiveness of Milo is not yet available, though RoboKind's claims that the robot has positive effects on joint attention and eye gaze behavior is consistent with that of SAR research in general and the robot's anthropomorphic design.

To date, robots used in autism and ASD therapy—even when intended to improve a subject's eye-gaze behavior—have not typically utilized animatronic eyes that duplicate the phenomenon, although some are programmed to exhibit some matter of gaze direction in the course of interacting with subjects. Two such robots are KASPAR, a product of the University of Hertfordshire; and FACE, a product of the University of Pisa. KASPAR, a humanoid robot about the size of a small boy, designed by its creators as "minimally expressive," has been the subject of SAR/autism-related research since the mid 2000s. Consistent with much SAR/autism-related research, KASPAR has been used as a "social mediator" (Scassellati, Admoni, and Matarić, 2012; Dautenhahn et al, 2009). More relevantly, KASPAR was involved in a series of studies in which the robot would play "peeka-boo" with subjects, a game that notably centers around eye contact, though without requiring any great degree of eye movement (Dautenhahn et al, 2009). FACE is also a humanoid robot, or more accurately, simply the head of one, and like KASPAR is capable of displaying emotions, though perhaps to a greater degree. FACE was also initially developed in the mid 2000s, and continues to be the subject of laboratory research, some of which has been related to autism (www.faceteam.it).

Robots otherwise capable of making eye contact—outside the context of autism therapy—have been created in laboratories since at least the 1990s. Several examples have been created in a laboratory setting at the MIT Media Lab by Professor Cynthia Breazeal and the Personal Robots Group. these would include each of three robots named as "Lexi", "Leonardo", and "Kismet". These robots often have been programmed to utilize their own robotic gaze in social interactions with people. As such, certain examples have been programmed to utilize eye gaze maneuvers to perform different functions in the context of conversation. For example, Kismet, when in the midst of a conversation where eye contact was obtained, was programmed to look to the side in order to "hold the floor" before speaking—presumably indicating to the interacting person that the robot was no longer attending to the person's speech/actions/communication, but was instead preparing to speak/communicate itself. Similarly, a gaze, by the robot, directed at a person interacting with it was intended to show that that person had the robot's attention (Breazeal, 2003).

One of the most relevant examples of robots intended to make eye contact is that of "Robotinho", a robot developed at the University of Bonn and introduced as an experiment in the role of a tour guide for children at the Deutsches Museum. Robotinho is notable, not simply for having animatronic eyes that make eye contact with people in its surroundings, but for doing so at a speed and fluidity that allows for significant engagement. Robotinho "focuses its attention on the person who has the highest importance, which means that it keeps eye-contact with this person. While focusing on one person, from time to time, [Robotinho] also looks into the direction of other people to involve them into a conversation." (Faber et al, 2009)

The invention described herein is an attempt to apply newly available technology to the problem of autism and ASD treatment. Some of what is described in this application would not have been possible five or ten years ago. Parts of it share some similarities with some of the aforementioned technologies, but this invention also brings a novel focus, design, and function as well. It is possible that it might be used in conjunction with some of the aforementioned treatment strategies, but it also is meant to act on its own, with an altogether different mode of action.

SUMMARY OF THE INVENTION

This invention is a therapy method for autism/ASD. The goal of the therapy is to instill in a child subject a degree of intrinsic motivation to make eye contact, with the hope that doing so will ultimately aid in the child's development by easing their interactions with caregivers that might otherwise help them. The therapy method aims to achieve this goal by exploiting a natural phenomenon—that given any cohort of people who are exposed to a concept, that a certain subset of those people will become interested in that concept—and in such pursuit, the therapy employs an artificial demonstration of eye contact using animatronic eyes that is intended to create in the subject a state of hyperawareness regarding the concept of eye contact. The therapy tools used to effect the demonstration are novel to this invention and also described in this application.

For the purposes of discussion, I refer to the method of action of these therapy tools—that method being central to the therapy itself—as Demonstration-Based Concept Suggestion (DBCS) and describe such DBCS analogously as an attempt to "advertise" to the child subject a topic of interest, that topic being eye contact. The response to this "advertisement" of eye contact is internal to the child's mind and assumed to be cumulative in its effect. The response includes first a greater awareness of the concept of eye contact, followed by a greater interest in the concept as well as a desire to engage in the activity. Ultimately, it is hoped that the child will take action on their own, action arising from a sort of intrinsic motivation, and initiate eye contact themselves. Manifestations of this response—and its definitive attribution to this particular therapy method—are assuredly difficult to measure in practice, but can only be imagined to be positive.

Notably, with regard to eye contact, DBCS is dissimilar to traditional autism/ASD treatment strategies. It is dissimilar to that of ABA-DTT, featuring no discrete trials, nor a focus on the subject's external behavior. DBCS is also dissimilar to child-driven/naturalistic strategies, featuring no legitimization of the child's interests or behaviors, and employing a display that is truly exceedingly artificial and purposefully so. Neither does DBCS attempt to provoke joint attention or socialization through the introduction of novel stimuli or dedicated therapy session protocols.

In addition to the therapy method itself, this invention concerns two embodiments of the aforementioned therapy tool. The first of these embodiments is, quite literally, a black box with animatronic eyes affixed to one side. Apart from the animatronic eyes, the box/device is largely featureless so as to avoid any characteristics that might distract subjects from the eye contact display. The second embodiment is a stuffed dog that is perhaps more along the lines of what is expected in a consumer product for children. In both embodiments, the animatronic eyes are programmed so as to exhibit similar behaviors, engaging subjects/children with occasional glances as well as extended eye contact under some circumstances. The method by which this is effected is novel to this invention and discussed in the subsection "Rules Governing Eye Movements".

BRIEF DESCRIPTION OF THE DIAGRAMS

FIG. 1 gives a general impression as to the outward appearance of embodiment one of the therapy tool: a rectangular box with eyeballs affixed to one side.

Figure 7:
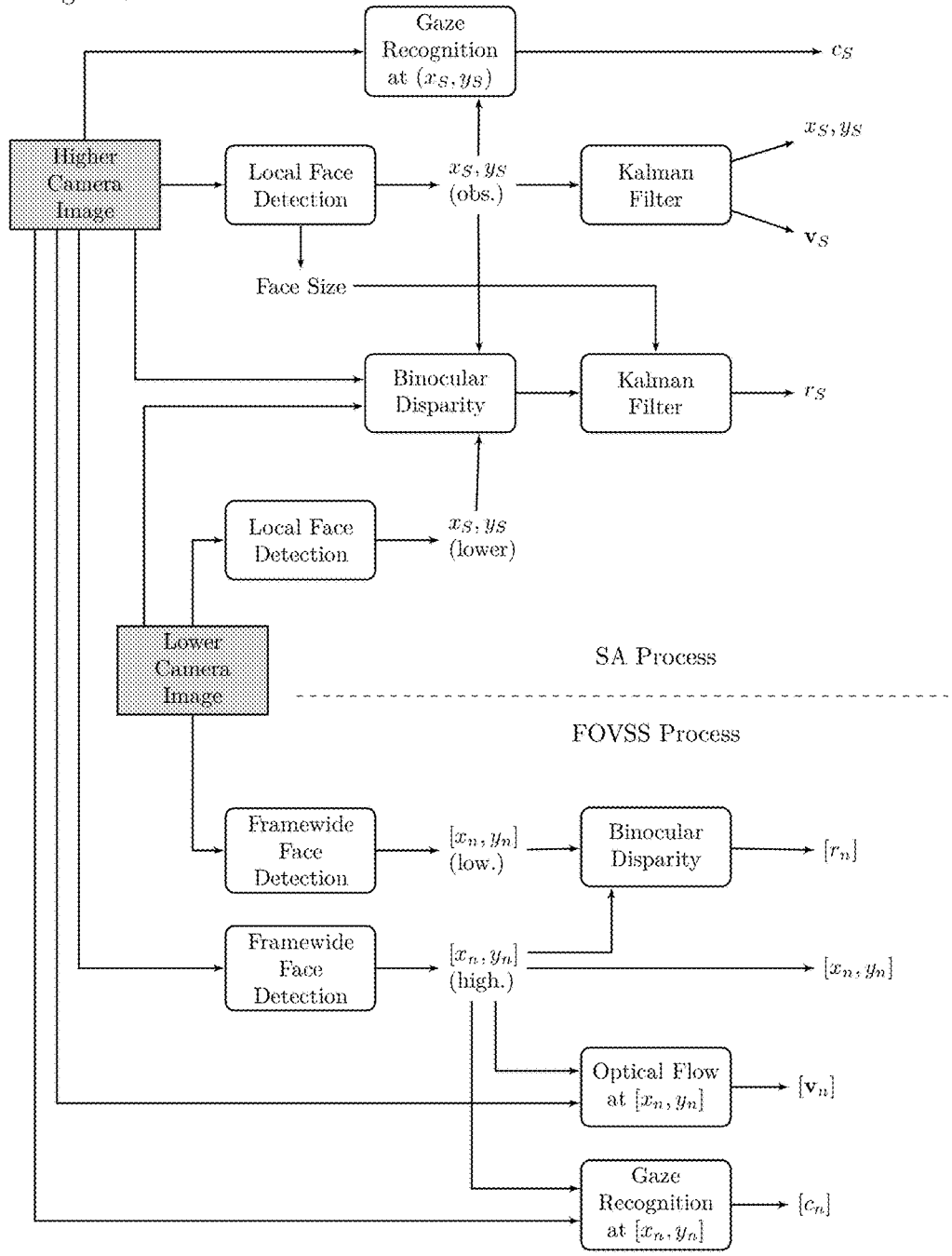

FIG. 7 diagrams two main software processes used to calculate intermediate variables central to the software used to direct the gaze of the animatronic eyes.

FIG. 8 provides a general impression as to the appearance and nature of the stuffed dog that is tool-embodiment two.

FIG. 9 is a cutaway diagram loosely depicting the placement of electronic components within the stuffed dog of tool-embodiment two.

FIG. 10 is a schematic showing the integration, within the dog of tool-embodiment two, of main process eye movement instructions—those derived from face detection, gaze detection, motion detection, etc.—with those instructions derived from the output of the accelerometer and gyroscope.

DETAILED DESCRIPTION OF THE INVENTION

Figure 1:
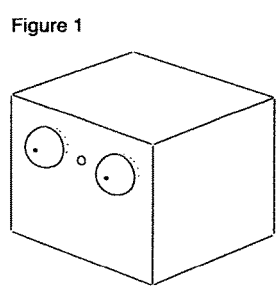

Here I begin the description of the therapy method by describing a particular therapy tool central to it. This tool, alternatively referred to in this specification as "the box", "the box/device", and "therapy tool-embodiment one", consists of a rectangular box of black acrylic, 12" wide, 12" deep, and 8" high. On the front side of the box is placed a pair of animatronic eyes, with two degrees of freedom in each eye's movement such that their apparent gaze can be directed in various directions. Between the eyes is located a camera capable of sensing video information available in front of the box. Several inches below this camera is a second camera thus allowing for stereopsis. These two cameras are designated the "higher" and "lower" cameras, respectively. In addition, the rear of the box has a power cord attached and a vent allowing the cooling of electronic and mechanical components located inside. Otherwise, the box is featureless, and purposefully so. A perspective view showing a general impression of the front of the box is shown in FIG. 1. (The location of the lower camera is not shown, but should otherwise be visible.)

Physical electronic and mechanical components inside used to animate the device are not claimed nor described in detail here, but can nonetheless be thought of as consisting of (1) a set of mechanisms powered by servos for directing the apparent gaze of the animatronic eyes, as well as (2) circuitry components that include, amongst other things, both a CPU and GPU as may be found on the commercially available NVIDIA Jetson TKI, and (3) a power supply, etc.

The animatronic eyes are not only capable of moving, but also capable of making eye contact with people in the immediate surroundings, and do so according to a specific novel set of rules described in the next subsection. In order to facilitate this, visual information as obtained by the cameras is processed internally such that the apparent gaze of the animatronic eyes can be directed accordingly. Importantly, the proscribed movements of the animatronic eyes are effected with both a relatively fast reaction time—reacting to new stimuli in under 20 milliseconds—as well as with rotation speeds fast enough to accurately mimic the saccades of human eyes, thus being on the order of 200° per second. Furthermore, the range of motion for the box's eyes is also similar to that of human eyes, albeit modified slightly. In general, human eyes have an ability to rotate side-to-side by about 450 of adduction/abduction, and a greater ability to rotate downward ("55°") than upward ("35°"). However, for this embodiment of the invention, the eyes are set to allow a range of motion of 50° through all four possible directions. This allows for the eyes to direct their apparent gaze more effectively to the side given that, unlike humans, the box cannot make a head turn, and upward to a greater degree of sursumduction, as it seems likely that the box should more often be placed below—rather than above—the eye level of those people in its surroundings. (To imagine this one might think of the box being placed on a table where people both seated and standing would be looking downward when looking at the box.)

It is no accident that this design eschews all prominent characteristics save for the animatronic eyes. The minimal and otherwise featureless design is specifically intended to draw attention to the only characteristics of note, the animatronic eyes. For the same reason, the box is indicated to have a dark exterior. It is purposeful that the dark exterior stands in stark contrast to the whites of the animatronic eyes. Importantly, these are functional aspects of the invention and not simply superficial, cosmetic characteristics. Inherently, the device is intended to highlight the phenomenon of eye contact to anyone who sees the device, and to some degree, this is accomplished by deemphasizing irrelevant aesthetic characteristics of the device, thus leaving only the eyes and their movements to remain as noteworthy.

The device is aided in its function of highlighting the concept of eye contact by the very powerful innate reaction that people have to eyes that reciprocate. Fundamentally, the ability to make eye contact is a very, very unusual characteristic to find in otherwise inanimate objects. In fact, the device of this specific design should be noted as having a potential greater ability to highlight the phenomenon of eye contact than do people or animals, living things that actually possess the natural ability to make such eye contact. In the natural world, including that of human civilization, the phenomenon of eye contact is only found when juxtaposed to numerous other prominent, interesting, noteworthy, and important characteristics. When confronted with another person in human-to-human interaction, eye contact is only one of many aspects of the interaction to consider, and such is also true of less complex interactions such as those involving animals. For example, when encountering a puppy, eye contact between the observer and the puppy may occur, but there are so many other interesting, notable attributes of the puppy—big eyes, wagging tail, playful nature, surprisingly sharp claws, etc.—that the observer is unlikely to actually think about eye contact even if eye contact is made. An artificial box, that eschews prominent characteristics save for its animatronic eyes, has a greater ability to highlight the behavior of eyes than do actual eyes in the natural world—including, and especially, those of other humans.

What is more, the attention of observers is brought to the phenomenon of eye contact by the box without any sort of linguistic explanation whatsoever, and this is highly valuable. The phenomenon of eye contact, itself, is of a very primal nature. It is fully recognizable between people of different cultures; it is fully recognizable between many species of the animal kingdom. It is also recognizable by developing infants long before they are able to understand language. And it is recognized by those challenged in their development so as to have severe and debilitating difficulties with communication.

Because of this unparalleled ability to highlight the concept of eye contact without any sort of verbal explanation whatsoever, this box/device must be seen as somewhat unique amongst tools that might be used in therapy related to autism. This uniqueness makes the box particularly interesting in the context of therapy, and it is not hard to imagine that it might be used both in the context of ABA—perhaps as a prop, a stimulus prompt—as well as in the context of alternative, child-directed, natural environment programs.

However, ultimately, the primary, intended use of this therapy tool is not in either of these contexts. Instead it is simply through its demonstration of eye contact that the tool/device is intended to act. In fact, the intended mechanism of action—this concept demonstration along with a subsequent and gradual afference of the concept of eye contact into the subject's mind—should not technically require the active participation of a therapist/caregiver. Instead, the invention is intended to perform its function in a way that is perhaps more akin to that of psychological suggestion (though admittedly only in the ideo-afferent sense, with only a delayed motor component). Through repeated, frequent, and obvious demonstration of the phenomenon of eye contact in a way that is wholly non-threatening, the device acts to induce in the subject a state of hyperawareness regarding eye contact with the hope that, over time, the subject may develop a newfound curiosity regarding that very concept of eye contact itself.

This mechanism of Demonstration-Based Concept Suggestion (DBCS) is perhaps best elaborated upon by means of an example.

Consider placing the device on an uncluttered shelf in a room where affected children might see the box/device often, but not for a long period of time on each occasion. I imagine a classroom used several times per week, or the waiting room at a therapist's office. Children, while they are intended to interact with it, are intended to do so only briefly, more than a few times, but only when it is convenient. Importantly, interacting with the box/device is their choice, though the device is hopefully placed where there is little else of interest surrounding it, so that it might be noticed. In this way, the box/device can easily perform its function of highlighting the concept of eye contact to any child who sees it, and the concept of eye contact is thus "advertised" repeatedly to the child. Such repeated "advertisement" will assuredly build within the child a greater awareness of the concept, and it is hoped that a greater interest will also follow.

Analogously, in this example, one might consider this box/device embodiment of the therapy tool to be something akin to a billboard—a billboard advertising to the children the very concept of eye contact. Encountering a billboard, a typical consumer/customer does not see it or consider it for a long period of time. Instead, one sees a billboard for only a brief moment every time that one drives by it on a nearby road. From an advertiser's point of view, the hope is that when the time is right, the consumer will then remember the advertisement, having seen it only briefly at any given time, yet still repeatedly. Here, the same is true for this device. The box/device will hopefully place into the child's mind a different way of thinking about eye contact—building awareness and interest, and hopefully, eventually, a desire and intrinsic motivation to engage with others in exploration of the concept. If the typical eye-contact-experience is daunting, onerous, tiresome, or frightening for the child, then the box/device—being wholly non-threatening—is intended to advertise it in a way that is not. The device should repeatedly remind the child of the very concept of eye contact itself-something that an interaction with another person wouldn't necessarily do given the pervasive juxtaposition of eye contact to all sorts of other experiential characteristics. And, hopefully, such a brief reminder—effected through DBCS—is enough so that when the child does happen to feel slightly more confident, slightly more inclined to try something new, and slightly more interested in exploring the nature of eye contact, when the right person is there for them to engage with, that child will actively, on their own volition, seek out the opportunity to engage in eye contact specifically, and see and experience the degree to which eye contact demonstrates and represents the inherent living quality of other people.

Consequently, it should be apparent that DBCS, the novel way that this invention is used when applied in- or out-of-therapy, differs substantially from established strategies. Although it is possible to conceive of the physical device being used as an antecedent prompt in the context of DTT, execution of "the billboard strategy" or DBCS in general is clearly not an implementation of ABA. Fundamentally, DBCS-use of the device does not request anything of the child, nor indicate that the child should engage in eye contact immediately or after a delay. It simply advertises the concept, and as such, DBCS-use of the device simply has very little in common with ABA's core antecedent-response-consequence framework. Nor is DBCS very similar to alternative strategies. While DBCS may seek to elicit a child-directed response, it seeks to do so without any imitation of the child and without any stated or unstated legitimization of the child's actions or behavior. DBCS seeks only to advertise a concept such that the child may consider it. While DBCS is not incompatible with NET, ultimately, there is very little that is natural about the device or its use. To the contrary, DBCS-use of the device is the direct introduction to the child of an object that is exceedingly artificial—an object that has had all of its secondary characteristics hacked away such that only a single characteristic remains. And while that characteristic of eye contact is found pervasively throughout the natural world, it is never, never found in isolation.

Thus as a novel technique for use regarding autism therapy, this example of DBCS-use of the physical device is specified as follows:

1. The device is placed such that the subject(s) comes into contact with it often, though never for a long duration. Notably, the general area around the device should be relatively free of distractions such that the device is sufficiently noticeable. In this way, the subject(s) has the opportunity, but not the obligation to interact with it.
2. The device through its operation and interaction with the subject(s) serves to highlight the phenomenon of eye contact to the subject(s), in a way that only a device so described can do so.
3. Given time for a subject(s) to consider the phenomenon, it is assumed that the resulting ideation regarding the concept of eye contact will differ from that derived from other stimuli. If successful, the child will exhibit an increased curiosity regarding eye contact, thus resulting in eye-gaze behavior that should not be subject to the "robotic" criticism of ABA results. Then, hopefully, when the time is right, the child will initiate eye contact on their own volition with newfound interest in the concept of eye contact and the way that people interact. It is at this point that any caregiver chosen as the object of the child's study should respond appropriately.

The exact manner in which a caregiver should act as the object in step three is, admittedly, less defined than the rest of the procedure. For practitioners of ABA, the first instinct may be to provide the child with a reward. And this provokes the question, should resulting DBCS—inspired eye contact from the child be reinforced?

Perhaps surprisingly, I believe that the answer to this question most in line with the spirit of DBCS is that the behavior should not be reinforced. Ultimately, when the child finally engages in DBCS-inspired eye contact, no reward should be necessary as the child is actively doing what the child wanted to do already. There should be no need to reward the child for a behavior that the child has chosen to effect in the pursuit their own curiosity. In fact, an inappropriate reward may, in such context, serve only to perpetuate the "robotic", impersonal, ABA-induced behavioral characteristics that parents tend to dislike.

Of course, in practice, the opportunity to reward a child for an overt and self-initiated display of engagement—if such success were to occur—may be an opportunity not to be missed, and of such action on the part of a caregiver, there can be no criticism. However, ultimately, DBCS does not call for an ABA-like consequence/reward in response to subsequent eye contact. Instead, given a positive DBCS result of child-initiated curiosity, the caregiver's course of action most in line with the spirit of DBCS would be relatively passive, with little to actually do than to simply be the object of the child's curiosity.

Rules Governing Eye Movements

Turning now to a more detailed description of the eyes' movement, while the animatronic eyes are intended to make eye contact with people in their surroundings, they are not intended to simply stare at those people. For the purposes of better drawing attention to the concept of eye contact, this invention uses a specific and novel state-based process that seeks to choose gaze directions based on several variables that are provided to it by other parts of the system software as needed. In broad terms, those variables are the following:

1. The location of the current subject in the Field of View (FOV) of the device, i.e. a set of coordinates $(x_S, y_S)$ designating the general direction of the subject.
2. The range to the subject, $r_S$, i.e. the distance between the device and the subject. Notably, from this value $r_S$ and the FOV coordinates $(x_S, y_S)$, it should be possible to calculate a specific set of Euler angles $(\alpha_L, \beta_L, \gamma_L)$ and $(\alpha_R, \beta_R, \gamma_R)$ through which each of the animatronic eyes left L and right R would need to rotate in order to make eye contact with the subject.
3. The speed and direction in which the subject is assessed to be moving, a vector $v_S$ upon the FOV.
4. A scalar variable $c_S$ indicating the level of certainty that the current subject is looking back at the cameras/box/device.
5. For secondary subjects numbered n=1 to N, coordinates $(x_n, y_n)$, ranges $r_n$, velocities $v_n$, and gaze certainties $c_n$ designating the locations, trajectories, and gaze qualities of other people in the FOV besides the primary subject.

Before proceeding to describe the eye movements and the principles behind them, I will better characterize the FOV as well as the related concept of the Field of Fixation (FOF). The FOV is defined as the entire area in which the cameras of the device can perceive the presence of the relevant subjects. For convenience in discussion, the FOV is not distinct for each eye or camera, but simply represents the overall area in which the box can "see". This field is coordinatized with two roughly rectangular dimensions x and y, which when combined with the range coordinate r, describe a space that maps one-to-one with the actual three-dimensional space in front of the box/device.

The FOF is related to the FOV, representing not the directions from which sensory information is available, but instead the set of directions to which the eyes of the box/device can be directed. By design the FOF is smaller than the FOV with the FOF's specifications as indicated earlier, corresponding to a circular solid angle of 50° in radius. Importantly, the FOV is intended to be somewhat larger than this FOF so as to allow some degree of peripheral vision, alerting the box/device to subjects that may soon be within its FOF even though it is not possible to direct the gaze of the box/device toward them.

Figure 2:
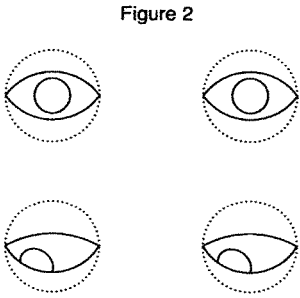
FIG. 2 shows five pairs of eyes that illustrate the general range of movement that the animatronic eyes have. (Importantly, while the shape of the eyes in these diagrams is affected by eyelids; eyelids are not required for the invention, but may, if included, add beneficial realism.)

The five pairs of eyes in FIG. 2 display something of the range of movements that the animatronic eyes are able to make. Notice that the eyes in this diagram change shape depending on their movements; this is due to the inclusion of eyelids. Eyelids are included here so as to add expressiveness, but are not essential to the design.

Now, proceeding with the description, I will start by addressing three situations/cases in which the eye's movements are important and representative.

1. A case in which a single, stationary subject is located in the FOF and is looking at the device with a certain, unchanging gaze.
2. A case in which a single, stationary subject is located in the FOF, with a gaze that can change over time, but not so as to look directly at the device.
3. A combination of cases one and two in which the gaze direction of a single, stationary subject varies, at times being directed towards the device, and at other times, being directed elsewhere.

Figure 3:
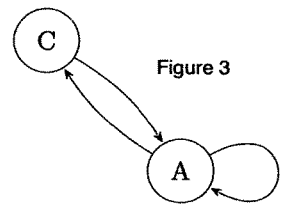
FIG. 3 is a directed graph depicting transitions concerning two possible computational states: state C indicating eye contact between the subject and the device, and state A indicating that the subject is looking at the device but that the device's gaze is averted.

FIG. 3 is a directed graph that shows the two possible states available to the device in case one. State C represents a state in which the device directs the gaze of the animatronic eyes back at the subject, and because the subject is here assumed to be staring at the device, state C represents eye contact. State A represents a state in which the animatronic eyes are directed in such a way that their gaze appears averted from that of the subject. Importantly, given a particular subject and subject location in the FOF, state C designates a particular gaze direction, whereas state A, on the other hand, represents many possible gaze directions. Edges in the directed graph in FIG. 3 represent saccades between these gaze directions. Notably, it is possible for the device to effect transitions both between states C and A, and also between an averted gaze in one direction to another averted gaze in a different direction, this represented by a loop connecting state A to itself.

Unlike state C in which the gaze direction of the device eyes is indicated specifically, additional logic is required in order to choose the actual gaze direction corresponding to a particular arrival at state A. For the purposes of doing so, gaze locations are further characterized by what I will refer to as their Relative Assertiveness (RA) whereby potential gaze directions in the FOF are assigned a scalar RA score based on a largely preset mathematical function.

The use of a mathematical function representing some characterization of relative assertiveness is inspired by some degree of relative assertiveness that seems present in human and animal gazes. It is a relatively common belief that a direct gaze of eye contact represents a degree of assertiveness and that an averted gaze is much less assertive and perhaps better-characterized as submissive. And although such assertiveness and submissiveness are not necessarily qualities that can be attributed to the box/device, such a quality of relative assertiveness is useful in providing a relative characterization of various gaze directions in order to better enable their selection.

Figure 4:
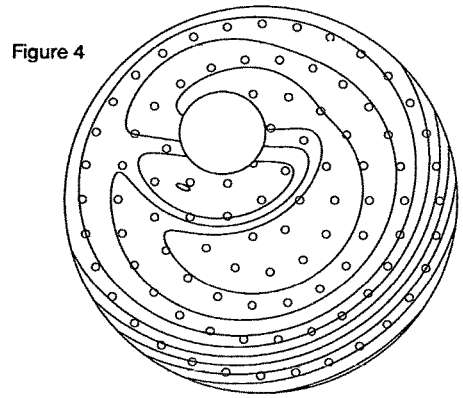
FIG. 4 is a contour graph displaying example relative assertiveness scores for gaze directed at various points within a given field of fixation (FOF), as seen from the device, given a single subject being present in that FOF and the gaze direction of that subject being toward the device.
Figure 4:
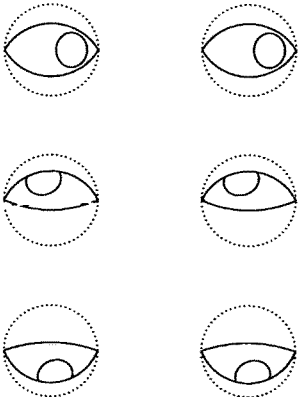

FIG. 4 is a contour graph that shows the RA scores as computed by the box/device for various gaze directions in the FOF. The largish, empty circle in the top-left quadrant of the graph/FOF indicates the location of the subject's eyes; gaze of the animatronic eyes directed at points within this circle is not considered to be averted as eye contact with the subject would then be possible. RA scores as depicted across other parts of the FOF take on values [−1, +1] and reflect several modeling assumptions: first, that the highest RA scores are seen just above the subject's head as well as toward the center of the FOF; second, that RA scores are lower just below the head/eyes of the subject; and third, that some of the lowest RA scores occur in the parts of the FOF that are furthest from the subject.

Also in FIG. 4 are represented ninety-eight sampling points across the FOF. The selection process in State A chooses primarily from the lowest quartile of such sampled values, but, otherwise, the choice is made largely at random. In this way, the relevance of RA scores is only in how they compare with other RA scores at one point in time. RA scores as computed here are not intended to be compared between frames, and in general, comparisons of such RA scores over time would only have limited meaning.

In general, these modeling assumptions relating to assertiveness are inspired by qualities of actual human-to-human interaction: first, that it is more assertive to look just above the head of someone with whom one is speaking with than just below; second, that all else equal, it is more assertive to simply gaze straight ahead than to avert one's gaze at all; and third, that the most submissive of gazes would be those that allow one to avert one's eyes to the greatest possible degree. Admittedly, although little more than intuition justifies these assumptions, they seem reasonable for their purpose, and seem to provide a reasonable function—the aforementioned RA function—that can be used to characterize the various gaze directions across the FOF possible for state A as well as in other states/situations yet to be described.

Thus, for case one, the behavior of the device is characterized entirely by these states A and C, and the order and timing of the transitions between them, A-C, C-A, and A-A.

The following quantities are used to further describe the timing of these transitions:

$t_C$, the length of time spent in state C after an A-C transition, $t_A$, the length of time spend in state A after either of a C-A or A-A transition, which are in turn used to define the three parameters by which to control the governing process:

$P_{A-C}$, the probability of an A-C transition given that one is already in state A, the alternative being, of course, $P_{A-A} = 1 - P_{A-C}$.

$\tau = (P_{A-C} \cdot t_C + t_A)/(2P_{A-C} + 1)$, a measure of the average time spent without changing from any particular gaze.

$\rho_{C/A} = t_C/t_A$, a measure denoting how much longer the average length of eye contact is relative to the time spent in independent averted gazes.

Informal study indicates that the τ values providing the most realistic feel are about three or four seconds, but can be set with lower values of one second or less—indicating a higher frequency of transition—for short periods as long as they decay to a more moderate level quickly. High τ values higher than four seconds are increasingly more boring. Low τ values for longer than a few seconds appear unnatural, sometimes greatly so.

τ values are set for the device stochastically via a mean-reverting Markov process such that they change gradually over time with the exception of some occasional jumps to lower values that quickly revert to values closer to three seconds that virtually never go above four. $P_{A-C}$ values are set randomly, except when low τ values are used, at which time a low $P_{A-C}$ of 0.1 or 0.2 is required. $\rho_{C/A}$ values are also set randomly, for the most part.

A final note regarding case one: in the event that the subject simply stares at the device for a considerable period, all three variables, $\rho_{C/A}$, $P_{A-C}$, and τ, are purposefully adjusted higher. This leads to the device returning the stare of the subject with any glances aside being brief and followed by a return to staring. In the context of the eye movements, I call this behavior "captivation" as it is intended that, despite some short-term variability, over time, the device is intended to be gradually drawn in—captivated—by the stare of the subject.

Figure 5:
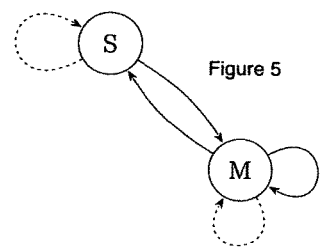
FIG. 5 is a directed graph depicting transitions concerning two possible computational states: state S indicating that the device is "looking" at the subject while the subject is looking away from the device, and state M indicating that the gazes of both the subject and the device are mutually averted.

FIG. 5 is a directed graph that shows the two possible states available to the device in case two. Case two is similar to case one except for the fact that the subject is, in this case, not looking at the box/device; the subject's gaze is directed elsewhere, but like case one, that gaze is unchanging. Similar to state C from case one, state S represents a state in which the box/device is "looking" at the subject. State M is similar to state A from case one in that the animatronic eyes are directed elsewhere from the subject to some other location in the FOF; state M thus represents a state in which both the subject's and the box's eyes are mutually averted. Unlike case one, case two also features two actions that are possible on the part of the subject—not the device—and these are represented in FIG. 5 by dashed self-loops. (For the purposes of notation, these loops are represented in this text as S~S and M~M, thus distinguishing the actions of the subject from those of the box/device such as in M-M.)

RA scoring is used in the selection of specific gaze directions on arrival to state M in much the same way as was described for arrivals to state A in case one. However, here, the selected gaze directions are not so heavily weighted towards those with extremely low RA scores. A wider variety is allowed, the mean/median scores being chosen to be higher, and this results in eye movement patterns that are less averted from the direction of the subject.

The transition rates are actually largely similar to those of case one, including occasional jumps to low τ values. However, "captivation" does not occur and there is no built in tendency for $\rho_{C/A}$, $\rho_{A-C}$, and r values to rise on average over time.

Figure 6:
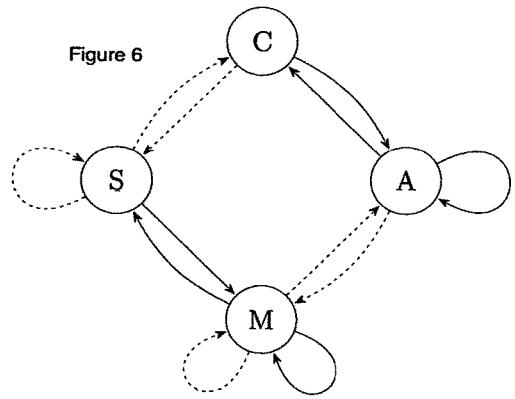
FIG. 6 is a directed graph that combines the graphs of FIG. 3 and FIG. 5, thus depicting all four computational states and all possible transitions between those states given the presence of a single stationary subject.

FIG. 6 is a directed graph that shows all of the four possible states of case three. Notably, for the most part, FIG. 6 is a combination of the graphs previously indicated in regards to states one and two, but with four new edges shown so as to represent transitions that can occur due to actions of the subject: C~S, S~C, A~M, and M~A.

What is most notable about case three is the reaction of the device to these actions of the subject, and to some degree the box/device actively acknowledges these actions. For example, given a new and relatively out of the blue S~C transition, the box/device, in short order, responds with C-A, and a jump to a low τ value. Periodic looks at the subject by the device are then appropriate, along with a gradual slowing of the animatronic eyes' movements over time, with greater and greater attention thus being paid to the subject. This is, of course, a manifestation of the "captivation" behavior of case one featuring increasing values for $P_{A-C}$, τ, and $\rho_{C/A}$. Similarly, the box/device acknowledges a relatively out of the blue M~A transition by effecting a low-τ jump, though it initially remains in state A. Behavior similar to that seen in case one then follows.

With regard to subject looks away from the device, a C~S transition is followed with an immediate S-M transition featuring a moderate τ value, a slightly increased $P_{M-S}$ value, and subsequent behavior similar to that of case two. Likewise, an A~M transition is also met with behavior like that of case two, though no abrupt, initial S-M transition is necessary.

Finally, while to some degree the behavior found in case three is something of a simple alternation between the aforedescribed behavior of cases one and two, the entire process is not entirely memoryless. Importantly, any gradual procession toward "captivation" that occurs because of time spent in states A and/or C is less impeded by brief moves to states M or S than memorylessness would imply. The degree to which the subject induces more frequent use of states A and C over states M and S is not immediately forgotten by the system, and the general use of A and C over M and S in the recent past causes the system to progress more quickly towards captivation. As any such progress towards captivation proceeds, so is greater attention paid to the subject not only when the subject is looking at the device, but also when the subject is looking away, and such is purposefully reflected in $P_{A-C}$, τ, and $\rho_{C/A}$ values following M-S and S~M transitions as appropriate. However, the prominence of this behavior on the part of the device is limited, and most importantly, without a subject-initiated return to states A and C, gradually diminishes over time.

The three aforementioned cases describe the behavior of the box/device in a limited variety of situations in which there is a single, stationary subject in the device's FOV. In order to define the remainder of device behavior, I will address how that behavior changes in response to three additional possibilities: (1) that there is uncertainty with regard to whether or not the subject is looking at the device, (2) that a subject is not stationary but is instead moving slowly or briskly, and (3) that more than one possible subject is present in the FOV.

Uncertainty regarding whether the subject is looking at the device—in the form of low $c_S$ scores-results in reduced use of states S and C in favor of greater use of states M and A, and this is effected through a general reduction in the values of $P_{A-C}$ and $P_{M-S}$.

Small amounts of movement from the subject are largely irrelevant. For the most part, the animatronic eyes of the box/device are directed in much the same way as they would be with a stationary subject with the only difference being that a moving subject is followed by the animatronic eyes of the device when in states C and S and thus in those states the eyes would not, themselves, be stationary. Updates made to the subject trajectory variables $x_S$, $y_S$, $r_S$, and $v_S$ by the underlying software processes make this function—as specified here-straightforward and, for the purposes of the rules governing eye movements, scarcely different than that regarding a stationary subject.

However, larger amounts of subject movement may result in a reduction in the quality of the device's sensory information, thus leading to both (I) greater uncertainty regarding the subject's gaze direction, i.e. lower $c_S$ values as reported by underlying software processes, and (2) greater error regarding those underlying software processes' estimates of $x_S$, $y_S$, $r_S$, and $v_S$. Any such increased error in $x_S$, $y_S$, $r_S$, and $v_S$ will hopefully be unnoticeable and otherwise minimized, but on the other hand, any reduction in $c_S$ values due to subject motion are intentionally reflected in eye movements in the same way that such lower $c_S$ values would otherwise be expected to be reflected: in general, with a favoring of states M and A over states S and C.

With the presence of two people in the FOV, box/device behavior remains similar, with one and only one of those two people being chosen to be the primary subject at a given point in time. Transitions between states C/A/S/M also remain similar and are determined primarily by the box/device's interaction with the primary subject alone. However, RA functions upon the FOF are computed such that the presence of the second subject is also taken into account. In general, the same principles of RA score calculation apply: that a direct gaze at either person would be relatively assertive, that a gaze above one a subject's head is more assertive than a gaze below, that the most submissive gazes are probably those in which the eyes of the device are averted to the greatest possible degree from both subjects, etc. In addition, in what might be called a "glance", an entry into either of states A or M also allows the choice of a direct gaze at the secondary subject to be selected as an "averted" gaze as long as the duration of stay in that A or M state is set to be suitably brief; such glances occur with probability $P_G$, but are more likely when $r_1$ is small and $c_1$ is large ($r_1$ and $c_1$ being variables that correspond to the one and only one secondary subject: n=1).

With some frequency, the device also assesses when it is appropriate to effect a subject-change from the current primary subject to that of the alternative. In order to facilitate this periodic decision, variables $x_1$, $y_1$, $r_1$, $v_1$, and $c_1$ are made available by underlying software processes. Most important to consider is the degree to which the current primary subject is paying attention to the box/device, i.e. engaging in states C and A. More engagement in these states reduces the likelihood of switching to the new primary subject. The assessment is cumulative, in a way, with consistent and recent C/A state engagement being most important, and with only less emphasis placed on whether or not the current state is C or A. Also, a high $c_1$ score increases the likelihood of choosing the alternative subject as this indicates that secondary subject is currently looking at the box. The probability is higher still if the recent history of the $c_1$ score has been high in general, thus indicating that the secondary subject has been looking at the box frequently.

With the presence of a third person in the FOV, device behavior remains similar, with one and only one of the three people in the FOV being chosen as the primary subject at any given time. RA scores reflect the presence of all three people. Low $r_n$ and high $c_n$ scores make a secondary subject n more likely to be chosen as either the next primary subject or for just a fleeting "glance." The recent history of $c_n$ scores—not just the current $c_n$ score—affects the likelihood that a particular secondary subject n will be chosen as the next primary. $P_G$ is somewhat greater with the presence of three people than two.

When the number of secondary subjects is small, the behavior of the box remains similar to that specified for the presence of one or two secondary subjects. However, ultimately, with somewhat more people present in the FOV, the FOF becomes crowded, and it becomes more difficult to specify a gaze direction that is suitably averted from all of the people present. Consequently, when the FOF is determined by device processes to have become too crowded to adequately represent the A and M states, the device responds with deliberately higher $P_G$ values, thus resulting in more quick glances to the eyes of secondary subjects in the FOF instead of averted gazes to relatively empty parts of the FOF. Ultimately, if numerous subjects are present covering most parts of the FOF, then the animatronic eyes cease to make averted gazes based on low RA scores entirely, and instead simply look periodically at each of the people present. As before, low $r_n$ scores and high $c_n$ scores make it more likely that a particular secondary subject n will be chosen for a glance or to become the next primary subject.

Subject Detection and Gaze Classification

Having concluded describing the general process and rules by which eye movements are determined, what follows is a brief discussion of the underlying software processes and their calculation of the "input variables" listed in the previous section: $x_S$, $y_S$, $r_S$, $v_S$, $c_S$, etc. FIG. 7 shows a flow diagram indicating the two necessary processes. The first, the Subject Analysis (SA) process, must locate the subject within a given frame, estimate the range to the subject, and, if necessary, recognize the subject's gaze if it is directed at the box/device. The second, the FOV Subject Survey (FOVSS) process, is tasked with locating additional possible subjects within a given frame, determining their direction of travel, the range to each, and assessing if any are looking at the box/device. Importantly, in general operation, with only one subject present, the SA process runs most frequently—hopefully, for each and every frame, although it is acceptable if frames are dropped. The FOVSS process runs only less frequently.

Notably, both of the above processes—SA and FOVSS-require face detection.

The problem of face detection, being one of the first addressed problems of artificial intelligence as far back as the 1960s (Zafeiriou et al, 2015 indicates Bledsoe and Chan, 1965), has been attacked with numerous different algorithms, some of which have risen to particular prominence as of 2016 such as those using the Viola-Jones object detection framework (Viola and Jones, 2001) and those using convolutional neural networks (Zafeiriou et al, 2015). Here, for neither of the SA nor FOVSS processes is any one particular face detection algorithm indicated; however, in general, it is important to choose an algorithm that will deliver strong performance given the characteristics of the problem. In the context of the SA process, it is necessary to allow for fairly quick location of the subject such that second stage gaze recognition can commence as soon as possible. In which context perhaps the most notable characteristic of the SA face detection task is that the relevant images are sourced from a video feed, and as such, there is a sequential continuity between them. Thus the location of the subject in one frame provides a good indication as to the general area where the subject may be found in the next frame. Optimizations based on this principle have been found highly effective in shortening both computation time and increasing the reliability of face detection. In a similar vein, searching frames for face shapes that are similar to the shapes representing the subject in previous frames is also likely helpful, particularly so given that the orientation of a person's head can change over time resulting in considerably different images representing even the same person. Other algorithms address aspects of similar face tracking problems that are indeed unnecessary here, such as those that aim to track specific facial features such as the nose, mouth, cheekbones, etc. (Milborrow and Nicolls, 2008). Of course, the chosen algorithm for the SA process should take advantage of the relevant characteristics of the problem, and avoid focus on unneeded features.

In the context of the FOVSS process, the same continuity between video frames is available, but because no particular subject has been previously identified, it is less practical to look for a subject in a specific location as the introduction of a new subject elsewhere might be missed altogether. Instead, a broad survey of each frame is reasonable and no such optimization is sought. One might expect this to cause the overall process to be too expensive computationally; however, conveniently, here the constraints of the task are less onerous than with the SA process. First, failure to find any particular face in any particular frame is not of great concern given that no particular subject is of particular interest, i.e. any subject will do. Second, the device is not tasked with reacting quickly to the actions of alternative, secondary, possible subjects, and consequently it is not necessary that the process run for each and every frame. Because of these relatively lax requirements, truly any decent face detection algorithm will work for this purpose. Ultimately, the very popular, tried and tested OpenCV implementation of the Viola-Jones algorithm may be a convenient choice.

The SA process is, of course, a two stage process, with the second stage being that of gaze recognition (GR), defined here as recognizing that a particular face in the FOV, already located, is looking at the device, and thus it is either making or inviting eye contact Although similar gaze analysis problems have often been addressed by researchers (Hennessey, Noureddin, and Lawrence, 2006 indicate Morimoto and Mimica, 2005), the problem of identifying specifically whether or not a subject is looking back at a computer's camera has not been a common/identifiable topic of published research. There are no off-the-shelf open source utilities to handle the problem. In fact, researchers indicate that similar—but perhaps somewhat more complex-problems are often considered quite challenging (Lu et al, 2011). However, ultimately, this second-stage GR problem is still a variation on the more common problem of image classification, and the simple output required here is not as complex as those sought by researchers of the more difficult "gaze tracking" problem.

Historically, image classification has been considered a difficult computer vision problem in general due to the difficulty of formulating a priori rules on which to base an algorithm. Because of this characteristic, the two most prominent and effective cutting-edge ways of approaching image classification—deep convolutional neural networks (DCNN) and support vector machines (SVM)—are both nonparametric and rely on training a relatively generic system that can learn iteratively the correct output behavior. These two approaches are certainly the best options from which to choose in order to solve this problem of gaze recognition.

Suggested characteristics of a DCNN constructed for the job would be those consistent with a similar system recently used at Microsoft for the purposes of determining head pose/orientation—i.e. the direction towards which a recognized head is turned—consisting of an initial face detection stage followed by subsequent processing by a DCNN "post-filter" (Zhang and Zhang, 2014). In Microsoft's system, cropped subimages containing facial close-ups arising after the initial face detection stage are resized to a standard 32×32 pixel format and analyzed by a DCNN trained on 1+ million facial images (about 120,000 original images plus various transpositions of those originals). The network itself consists of a 5×5×1 convolutional layer, followed by a max pooling layer, more convolutional layers, and finally a fully connected layer.

The exact specifications of a DCNN are typically massaged by the builders until the problem is solved satisfactorily, and notably, the here problem of gaze recognition differs slightly from that of head pose/orientation estimation as faced by Microsoft. Making the here problem of gaze recognition harder is the fact that the cropped image features that might indicate whether a person is looking at the box/device—i.e. whether their pupils are pointed in the right direction—are far more subtle than those that would denote head pose/orientation. As such, data reduction techniques such as principal component analysis that can be used to reduce the dimensionality of other problems may be less effective here, as focusing on "low-frequency" components of the input images would likely prove insufficient; this may mean that the "volume" of a networks hidden layers must be larger, using more kernels. It may also be necessary to use larger input images as well, e.g. cropped, scaled facial images of 64×64 pixels, instead of the popular 32×32 format. Such a change in the size of the input images would likely require similar adjustments broadening the sizes of subsequent network layers and requiring that aggregation layers operate over larger areas. It may also be necessary to use more training images; this reflects the assumptions of some researchers addressing similar—but notably more complex—problems, that have referred to the number of required training images for "gaze tracking" to be "prohibitively" high (Lu et al, 2011). On the other hand, making this here problem of gaze recognition easier is the fact that the answer to whether or not a particular person is looking at the device is ultimately boolean and a simple yes or no answer will suffice.

Both DCNN and SVM take advantage of parallel computation in order to solve image classification problems, and as such, the performance of each is improved by using hardware capable of exploiting this characteristic. Consequently, the box that is this first embodiment of the therapy tool uses a Graphics Processing Unit (GPU) in order to allow gaze recognition routines to run as fast as possible. Such use speeds not only the running of the DCNN, but also the execution of the Viola-Jones algorithm suggested for face detection, as well as many other relevant computer vision processes. It is notable that the relevant hardware for these purposes-such as the NVIDIA Jetson TKI as mentioned earlier—is commercially available and that the use of the GPU component on that specified NVIDIA product by Intel's OpenCV can be facilitated using NVIDIA's CUDA platform.

This same DCNN utility described above can also be used, when appropriate, to recognize the gaze of other possible subjects, not simply that of primary focus, and such information is made available to the aforedescribed algorithm based on the relative assertiveness of gazes in the form of N variables numbered 1 to N, $c_1$ to $c_N$, for the purposes of governing the eye movements. However, it should also be noted that calculation of a full set of $c_n$ values $c_1$ to $c_N$ is probably unnecessary in pursuit of the relevant therapeutic goals.

The subject's velocity $v_S$ upon the FOF/FOV is estimated using a Kalman filter. This allows the integration of current observational data regarding the current location of the subject from the SA process, $(x_S, y_S)$, to be combined with a priori velocity estimates based on the data from previous observations. This process is robust in the event that results from a small number of frames must be dropped from the data sequence. That the time between frames is not constant will not prevent the calculation of a reasonable and mathematically smooth subject trajectory and projected subject locations. Furthermore, while some errors in subject identification are likely when multiple people are present in close proximity to the subject, such is not expected often enough to affect the outward behavior of the device in a notably detrimental way.

A rectangular xy-coordinatization of the FOV/FOF is used rather than one that is polar-based—something that might seem counterintuitive given that the animatronic eyes rotate to direct their gaze, and of course, do so through amounts measured as angles. Such is more convenient for use with the Kalman filter making trajectory estimation less error prone given that the basis vectors for such an xy-coordinatization are more consistent and not subject to great variation around any pole/zenith.

Velocities $v_1$ to $v_N$ for secondary subjects n=1 to N are performed quite differently than the analogous calculations for $v_S$ regarding the primary subject. The reason for this is not related so much to the added computational expense as it is to the fact that these secondary subjects are not tracked from one frame to the next like the primary subject is and thus determining which detected secondary face corresponds to which from prior frames is problematic. Some faces detected in one frame may not even be detected at all in others causing significant complications with regard to determining their correspondence. Better is simply measuring the optical flow in the regions of each face. Such is certainly an imperfect measure, but does allow estimating the velocity of each detected face without relying on information in other frames in order to do so.

Algorithms that calculate the optical flow over the entirety of a frame such as those of Lucas-Kanade (Lucas and Kanade, 1981) and Horn-Schunck (Horn and Schunck, 1981) can usually do so only slowly. Clearly, in this case, doing so over the entire frame is not necessary given that the location of each face is known beforehand, and instead, execution is only performed local to any given face of particular interest, and even then, only when necessary. Again, Intel's OpenCV may be useful in this context and the choice of the NVIDIA platform is also appropriate.

Range values $r_S$ indicating the amount of physical distance that separates the device/box and the subject are calculated using a Kalman filter integrating information from two sources: (1) the size of the subject's face as it appears in the FOV as determined by the SA process, and (2) coincidence rangefinding given stereoscopic information from each of the higher and lower cameras. Notably, the size of the subject's face as indicated by the SA process is available as a byproduct of the same face tracking operation that indicates $(x_S, y_S)$, and as such it is available frequently and at very little additional computational cost. On the other hand, this information alone is not sufficient to determine subject range. For example, while adult human head sizes vary within a more narrow range than one might otherwise expect—the 99th percentile being only about 20% to 30% larger than the 1st—child head sizes vary considerably given age and differ significantly from those of adults. Another complicating issue is the fact that if the subject makes a head turn orienting, thus, in a different direction, the chosen face detection/tracking algorithm may register a different size, even for the same person at a given range. Consequently, while face size is seen as a possible means of updating the range coordinate $r_S$ from frame to frame with little other information, stereo correspondence information from the cameras is also incorporated when possible in order to improve the estimate, as well as to simply calibrate it given that the face sizes of individuals varies.

In coincidence range finding, image depth and subject range are inversely proportional to the binocular disparity as measured in pixels of displacement. For this general problem, and related problems, many, many different algorithms and solutions have been developed, some focusing on the edges between regions of different depths, others on the "dense" problem of computing the pixel disparity for each and every pixel of a region (Scharstein and Szeliski, 2002), and yet, others being optimized for targets that are mere points in a camera's FOV. However, despite the significant research that has gone into the problem, stereo correspondence algorithms that operate over the entirety of an entire frame remain quite time-consuming, and consequently, it is fortunate that estimating $r_S$ is less critical than estimating other more important variables such as $(x_S, y_S)$.

If development finds that relatively infrequent stereopsic assessment is insufficient, then some aspects of the here problem will allow for improvements in computation time. Just as the SA process face detection algorithm can be improved by taking into account the temporal continuity between video frames, so can the same temporal continuity be taken advantage of in order to guess the subject range; prior knowledge of where the subject appears in an image sourced from the upper camera allows a guess—given a prior range estimate—as to where the subject should appear in the corresponding frame from the lower camera. Consequently, minimizing the sum of squared differences in pixel intensity may be a fairly quick process as the initial guess may be fairly good. A good guess as to the subject location in the lower camera's frame, and a subsequent discovery that, in that region, the gradient of the SSD function with respect to the binocular disparity in pixels is low or near zero, may be enough to provide a reasonable $r_S$ value. What is more, this stereopsic assessment need not be performed for the entire frame, but only in the region of the subject. Of course, such customized development is hopefully unnecessary.

Rangefinding for secondary subjects is somewhat different. Similar to $v_n$ values, it is not clear that calculation of numerous $r_n$ values will be greatly beneficial. If so, then they may be calculated similarly to $r_S$ though it must be assumed that face size data will be significantly less predictive given the difficulty of determining temporal correspondence between face detections. Possible solutions would include a simple assumption that the head sizes of people in a given frame are all the same as those of the subject—introducing some error given that the head sizes of children can be half that of adults—or a simple decision to only rely on the stereo correspondence information for the purposes of calculating $r_n$ values, which would, of course, limit the frequency with which $r_n$ values could be updated.

Therapy Tool Embodiment Two

A second embodiment of the therapy tool consists of a simple stuffed dog that features animatronic eyes capable of making eye contact in much the same way as do the animatronic eyes of the first embodiment. FIG. 8 displays an impression of this stuffed dog, the dog being approximately one foot in length, front paws to tip-of-tail. Notably, the eyes are quite prominent as part of the dog's aesthetic design.

Similar to the box of tool-embodiment one, the dog of tool-embodiment two eschews unnecessary secondary characteristics with the aim of drawing people's attention to its eyes (although notably to a lesser degree). Save for the dog's eyes, the dog has no moving external parts. The dog makes no sounds: no barks, howls, or anthropomorphic vocalizations. The dog's coat should be of a simple design: probably a solid color, perhaps dark, and certainly not a detailed spotty pattern that would present little contrast to the eyes.

These design choices reflect the same goals driving the minimal design of tool-embodiment one: that the purpose of the device is to highlight the concept of eye contact and that this is best done by a device that eschews irrelevant characteristics. Obviously, the dog of tool-embodiment two is a less pure realization of this. However, the sacrifice here is with purpose, two-fold: first, to realize the tool/device such that a child of exceedingly young age may be allowed to hold and handle it at will, and second, to realize the tool/device in a form that people commonly see as appropriate for children. As such, the dog of tool-embodiment two sacrifices some degree of minimalism in favor of being soft, portable, cute, as well as child-safe to the point that a toddler or infant might be allowed to gnaw on it without danger.

FIG. 9 displays a cutaway diagram of the dog of tool-embodiment two. Not intended to be a detailed depiction of the dog's interior, this diagram of FIG. 9 simply indicates the general location of two electronic components within the dog that are together joined by a multichannel wire. One component that I will call the "eye assembly" or "animatronic eye assembly" is located in the head, and this component includes the animatronic eyes as well as the accelerometer and gyroscope intended to measure the dog's rotational and translational movements. Notably, this first component is affixed to the exterior of the dog using a rigid bracket that is capable of holding the component in place such that the eyeballs are appropriately aligned with the eyeholes of the "stuffed-dog-body," i.e. the stuffing and outer skin comprising the legs, tail, ears, and, in general, the soft, furry, plush exterior of the dog. The second component, which I will call the "processor assembly," is slightly larger and is located within the chest/belly of the dog. It houses all processing components, CPU, GPU, RAM, and flash memory, as well as the battery. Also notable is the presence of a camera in the nose of the dog, and that this nose tip device is affixed firmly and directly to the anterior portion of the same rigid bracket that holds the eye assembly in place. Importantly, it is possible to remove all three of these electronic components from the stuffed-dog-body such that the body can be machine-washed or replaced if it becomes soiled or excessively worn.

The function of the rigid bracket in the snout of the dog is threefold. First, to hold the animatronic eyes in place relative to the eyeholes of the dog. Second, to hold the camera in the nose of the dog in rigid alignment with two cameras placed within the animatronic eyes themselves. And third, to facilitate the passage of power and communication channels to the nose tip camera, that camera being otherwise separated from all other electronic components including the battery. In order to perform this third function, the rigid bracket is equipped with some form of wire that passes along its length, either interior to the bracket, or affixed to one side.

The function of the dog of tool-embodiment two is much the same as the box of tool-embodiment one. The dog is intended to, via DBCS, induce in an affected child—perhaps one of very young age—an enhanced awareness of, interest in, and curiosity regarding eye movements and the concept/phenomenon of eye contact, specifically. As before, it is ultimately hoped that, over time, such increased awareness and interest will lead to an increased desire—a degree of intrinsic motivation—to participate and engage others in such eye contact.

Construction of the stuffed dog of tool-embodiment two is substantially more complicated than the box of tool-embodiment one due to several reasons. First, space within the dog is limited. In order to fit within the dog, both the eye and processor assemblies must be quite small, and this means that the battery, processors, and memory, etc., as well as the eye movement mechanisms and other parts must fit within a much smaller space. Second, a greater energy efficiency is required. In the case of the box, it is assumed that the device might be plugged into a wall outlet. However, the dog must rely on battery power. This places considerable constraint on the design of the animatronic eyes, as physical movement of the eyes is assumed to occur with great frequency and all angular acceleration must be effected using energy sourced from the battery. Third, a greater standard of durability is necessary. In order to derive the dog's intended benefits, its use cannot be limited to it being viewed upon a shelf. Instead the dog must be suitable for children to handle directly, and as such, the dog must capable of withstanding occasional impacts due to—for example—being thrown from one side of the room to the other. Fourth, the dog's design must also solve what might be called the Vestibulo-Ocular Reflex (VOR) problem, a problem that in this context is defined as that problem concerning the ability of the stuffed dog's animatronic eyes to remain fixated on a particular point in space—particularly that corresponding to the eyes of a person with which it is engaged in eye contact—given any rotational or translational movement of the dog/tool.

In order to tackle these considerable necessities of (1) compactness, (2) efficiency, (3) durability, and (4) solving the VOR problem, the design of this stuffed dog of tool-embodiment two employs the animatronic eye design of U.S. Pat. No. 8,715,033, thus keeping the number of moving parts to a minimum, while simultaneously being lightweight and efficient. The reader is referred to that patent for greater detail. Very generally, the eye design of that patent consists of three concentric spheres: a clear plastic inner sphere and a clear plastic outer sphere, each connected to the other at the back of the eye, with a transparent fluid located between them, and suspended in the fluid a third sphere—actually a hemisphere—that is free to move from one side to the other as well as up and down. It is on this middle sphere on which the "eye graphic"—a white portion, as well as colored iris—is painted, and this middle sphere being eggshell-thin, is driven in its motion within the fluid by a set of four permanent magnets attached to it, each magnet located at 90° from the location of the pupil, and 90° from the nearest magnet. The magnets on the middle (hemi-)sphere are acted upon by electromagnets located on the outside of the outer sphere—also located at roughly 900 from the pupil and 90° from each other—and it is through the variable control of these exterior electromagnetic magnets that the eye graphic painted on the middle (hemi-)sphere may be directed this way and that.

The animatronic eye design of U.S. Pat. No. 8,715,033 also features a camera in the center of the eye. Visual input to the camera is obscured by the opaque painting on the middle sphere of the iris and white of the eye graphic. However the pupil of the middle (hemi-)sphere is transparent, as are the inner and outer spheres as well as the suspension fluid, and thus, the camera is able to "see" through the pupil. Importantly, the camera of this animatronic eye design does not move with the directed gaze of the eye, and the narrow tunnel of vision possible for each animatronic eye moves as a circle across the internal camera's FOV.

Ultimately, in this eye design, the eggshell-thin middle (hemi-)sphere is the only moving part. Being so thin, the middle (hemi-)sphere's moment of inertia is tiny, and this, in addition to the fact that its movement as suspended in the fluid is virtually frictionless, means that even its quick and frequent acceleration places only minimal demand on battery resources. Because no unusual stresses are placed upon this single moving part, and the only other components are the rather unbreakable electromagnets and enclosing plastic spheres, this design is just about as durable as can be imagined given the requirements and far more durable than the circuitry that is otherwise required for the stuffed dog tool-embodiment. Furthermore, due to the compactness of the electromagnetic drive—consisting only of four, relatively small electromagnets—the entire eye assembly for the dog need only be scarcely bigger than the dog's eyeballs themselves, an accelerometer and gyroscope easily fitting into the posterior portion of the eye assembly.

It should also be noted that the use of a nontoxic suspension fluid will ensure product safety given handling of the dog by very young children, and because the only moving parts of the eyes are housed within the protective outer plastic spheres, any force put on the dog's exterior through normal play should not prove damaging as it might be if there were external, moving pieces. Thus, the use of the U.S. Pat. No. 8,715,033 eye design along with a nontoxic suspension fluid ensures that the eyeballs themselves are of comparatively less concern in ensuring product safety than the internal circuitry components, such circuitry components being not unlike those of a myriad of electronic stuffed toys in the marketplace and for which established manufacturing safety standards/procedures/protocols already exist.

Also, due to the middle (hemi-)sphere's low moment of inertia combined with the inherent efficiency of using an electromagnetic drive, the design is also useful in solving the VOR problem.

In people, the VOR—that reflex that allows people to maintain gaze upon a fixed point as the head rotates—is necessarily effected by the contraction/relaxation of the muscles surrounding the eye. Medical science has determined that, in people, this reflex is necessarily effected in response to sensations in the inner ear that are caused due to changes in head orientation and head acceleration, and that this VOR response actually occurs faster than it is possible for human eyes to detect changes in motion visually. Interestingly, such would also be true for electronic components given today's technology, and in order to solve the VOR problem, this design of tool-embodiment two "short-circuits" a "reflex" response in the eye movements directly to the detected motion originating from an accelerometer and gyroscope located in the animatronic eye assembly, bypassing software aimed at face detection, gaze detection, motion detection, etc., that is otherwise the focus of most of the computational components.

FIG. 10 displays a schematic that displays the general process by which the dog's apparent gaze is determined. The circular shapes toward the bottom represent software processes that run on the hardware located in the processor assembly; these include each of the SA and FOVSS processes (marked accordingly), as well as their Kalman filter subprocesses (each marked as "KF"), and an implementation of the rules as were described in the subsection of this document "Rules Governing Eye Movements" (marked "Rules"). Above those is a section indicating the comprising components of the eye assembly: the accelerometer (marked as "Acc."), the gyroscope (marked as "Gyr."), and the two animatronic eyes. Above these is depicted the nose of the toy including the nose-tip camera. And at the very top of the diagram is represented the subject to which the dog/tool's attention is directed.

Incoming data from the accelerometer and gyroscope is immediately processed to give the best possible indication as to the rotational and translational movement of the toy through three-dimensional space. No compass is included as the permanent and electromagnetic components of the animatronic eyes would cause sufficient field disturbances so as to render it useless. Quick re-estimation of $(x_S, y_S)$ and $v_S$ is effected in response to accelerometer and gyroscope output in the same Kalman filter as used by the SA Process, and as such these estimates are also corrected periodically by the more definitive information being computed by the higher-level SA-process vision components. In effect, this process allows the gaze of the dog/tool to be adjusted as fast as information from the accelerometer/gyroscope becomes available. Consequently, most of the time, between frames/assessments by the higher-level functions, the gaze direction of the dog/tool is actually selected via a comparison of a prior indication of the subject's location/velocity in/upon the FOF/FOV and more frequent updates to dog/tool-orientation data as provided by the accelerometer and gyroscope.

For this second tool-embodiment, coordinatization of the FOF/FOV using xy-coordinates remains more convenient than using polar coordinates.

Image data arrives for processing at the processor assembly from three sources: one video camera that is affixed to the stuffed dog's nose, and two cameras—one located in each animatronic eye—as are found as part of U.S. Pat. No. 8,715,033. Notably, there is a significant quality difference between these feeds, as the eyes' video capability is impaired in two ways. First, the internal eye cameras' views are impeded by both the plastic of the inner and outer spheres as well as by the fluid between them. And although these portions of each eye are intended to be as transparent as possible, they are presumably still subject to the effects of small deformities in the plastic. Such deformities are likely very difficult to remove entirely given the need to keep production costs low while ensuring that there is an absolute minimal possibility of shatter. Ultimately, the distance between the inner and outer spheres is only held steady by the joining of the spheres towards the rear of each animatronic eye, and even if the refractive index of the internal fluid is carefully matched with the plastic's refractive index, the video quality as provided by these cameras' remains impaired as the width of this fluid layer will be subject to any slight manufacturing deformity as well as those that might arise due pressure through normal play as well as changes in temperature. Presumably, these reasons are the cause of the reduced image quality as seen in photos taken by a prototype as distributed by the inventors (Bassett, Hammond, Smoot, 2009).

Second, as mentioned before, the FOV of the eye cameras is also obscured by the painted eye white and iris portions of the eye graphic on the eggshell-thin middle sphere. In regions outside the pupil, this obscuration is to opacity, and thus it is only in a narrow region of the FOV in which the images from these cameras can be used. This means that only a small portion of the internal cameras' image sensors can be used at any given time, and thus the pixel resolution available for any given image is simply less that it otherwise would be were the cameras' FOV more efficiently used.

In comparison, image data that arrives from the nose camera is not compromised in these ways. However, given the nose's location several centimeters away from the animatronic eyes, and the fact that stuffed toys in general are often played with in very close proximity to the children's eyes intended to view them—perhaps only a few inches or less—the resulting parallax errors will often be immense. Consequently, this particular trinocular arrangement results in the situation in which two sets of images are available: (1) images sourced from the animatronic eyes themselves, that while free of parallax errors, are only useful in the assessment of nearby subjects as their resolution is quite low, and (2) images sourced from the nose tip camera that have a substantially higher resolution and are thus able to assess faraway objects well, but for which substantial parallax errors will interfere with the assessment of the nearby subjects. The use of these two relatively imperfect video sources by the dog of tool-embodiment two (one low-resolution, binocular source comprised of the eye cameras together, and a supplementary, high-resolution monocular source, i.e. that of the nose tip camera alone) contrasts with the more standard setup used by the box of tool-embodiment one (one relatively high-resolution binocular camera arrangement).

However, despite the differences, vision processing in the dog of tool-embodiment two remains substantially similar to that in the box of tool-embodiment one. Notably, processing is performed using each of two main processes—an SA process and an FOVSS process—and the components of each are substantially similar to the similarly-named processes in the box.

In the context of the FOVSS process, faraway faces are detected in the image sourced from the nose tip camera, and nearby faces in each of two images sourced from each of the eye cameras. The problem of determining facial correspondence between feeds is thus more complicated than in tool-embodiment one, yet remains conceptually similar.

Face tracking by the SA process is, of course, complicated by the use of two feeds. Beyond a certain preset distance from the device $d_{far}$, analysis of the subject can proceed simply with information derived solely from the monocular nose-tip feed; and within a certain preset distance, $d_{near}$, analysis can proceed with information derived from the binocular eye cameras. However, between these two distances—given that, by design, $d_{near} < d_{far}$—there is a middle ground in which the SA process must determine which information should be used for the task.

Combining data from the two feeds when the subject is judged between $d_{near}$ and $d_{far}$ is accomplished using the same Kalman filter used to "short-circuit" accelerometer and gyroscope input into the calculation. This results in the necessary trajectory-related variables for the subject: $x_S$, $y_S$, $r_S$, and $v_S$.

Gaze recognition, i.e. the calculation of $c_S$, is only performed on a single cropped face image chosen from either the high-resolution nose tip feed or one of the eye camera feeds, but not both. If $r_S < d_{near}$, the cropped, say, 32×32 face image is chosen from the binocular eye setup, chosen from one of the two eye cameras. If $r_S > d_{far}$, the cropped face image is chosen from the monocular nose tip feed. If $d_{near} < r_S < d_{far}$, and as long as the subject has been detected in each of the high-resolution monocular and low-resolution binocular feeds, then a choice is made as to which to use, and this choice is made so as to minimize discontinuity in the sequence. Thus, if a faraway subject comes closer, the choice will be for the high-res monocular source for as long as possible until either the subject is too close or that image otherwise becomes unavailable; at which point a switch is made to the low-res binocular source. Likewise, once chosen, the low-res binocular source will be chosen as the source for the, say 32×32 subject image for as long as possible, etc.

As indicated earlier, values ($x_n$, $y_n$) for subjects n=1 to N, if needed, are calculated for each of the monocular and binocular feeds and the results compared to obtain the best estimates given any constraints on computation time.

Range values $r_n$ for subjects n=1 to N, if needed, are estimated using (1) face size for faraway subjects using data from the high-resolution monocular feed, (2) stereopsic assessment and binocular disparity for nearby subjects using data from the low-resolution binocular feed, and (3) a combination of these two methods for subjects of intermediate ranges where appropriate.

Velocities $v_n$ for subjects n=1 to N, if needed, are calculated in the same way for the dog of tool-embodiment two as for the box of tool-embodiment one with the only caveat being that for subjects for which correspondence has been identified, the results must either be aggregated or one result discarded due to range.

Gaze certainties $c_n$ for subjects n=1 to N, if needed, are calculated in the same way here as they were for the box of tool-embodiment one. When correspondence is found, then a quick choice must be made as to which source to use as input to the GR DCNN.

REFERENCES (1) Bassett, Katie, Marcus Hammond, and Lanny Smoot (2009). "A Fluid-Suspension, Electromagnetically Driven Eye with Video Capability for Animatronic Applications." *Proceedings of the 9th IEEE-RAS International Conference on Humanoid Robots*, December 2009, *Paris, France*, pp. 40-46.

(2) Boyd, Brian A., Samuel L. Odom, Betsy P. Humphreys, and Ann M. Sam (2010). "Infants and Toddlers With Autism Spectrum Disorder: Early Identification and Early Intervention." *Journal of Early Intervention*, 32(2), 75-98.

(3) Bledsoe, W. W., and H. Chan (1965). "A Man-Machine Facial Recognition System: Some Preliminary Results." Technical Report PRI 19A, Panoramic Research, Inc., Palo Alto, Calif.

(4) Breazeal, Cynthia (2003). "Toward Sociable Robots." *Robotics and Autonomous Systems*, 42, 167-175.

(5) Brown, Gary, and Bob Bradley (2014). *ABA Programs for Kids with Autism: A Guide for Parents and Caregivers*. Amazon Digital Services, LLC.

(6) Cabibihan, John-John, Hifza Javed, Marcelo Ang Jr., and Sharifah Mariam Aljunied (2013). "Why Robots? A Survey on the Roles and Benefits of Social Robots for the Therapy of Children with Autism." *International Journal of Social Robotics*, 5(4), 593-618.

(7) Carbone, Vincent J., Leigh O'Brien, Emily J. Sweeney-Kerwin, and Kristin M. Albert (2013). "Teaching Eye Contact to Children with Autism: A Conceptual Analysis and Single Case Study", *Education and Treatment of Children*, 36(2), 139-159.

(8) Dawson, Michelle (2004). "The Misbehaviour of Behaviourists: Ethical Challenges to the Autism-ABA Industry." Self-published at Research Autism, www.researchautism.net.

(9) Faber, Felix, Maren Bennewitz, Clemens Eppner, Attila Go6rg, Christoph Gonsior, Dominik Joho, Michael Schreiber, and Sven Behnke (2009). "The Humanoid Museum Tour Guide Robotinho." *Proceedings of the IEEE International Symposium on Robot and Human Interactive Communication (RO-MAN)*, September 2009, Toyama, Japan, pp. 891-896.

(10) Foxx, R. M. (1977). "Attention Training: The Use of Overcorrection Avoidance to Increase the Eye Contact of Autistic and Retarded Children." *Journal of Applied Behavior Analysis*, 10, 489-499.

(11) Foxx, Richard M. (2005). "Severe Aggressive and Self-Destructive Behavior: The Myth of the Nonaversive Treatment of Severe Behavior." *Controversial Therapies for Developmental Disabilities: Fad, Fashion, and Science in Professional Practice*, Lawrence Erlbaum Associates, Inc., Mahwah, N.J.

(12) Francis, K. (2005). "Autism Interventions: A Critical Update." *Developmental Medicine & Child Neurology*, 47, 493-499.

(13) Gentry, T., et al., (2010). "Personal Digital Assistants as Cognitive Aids for High School Students with Autism: Results of a Community-based Trial." *Journal of Vocational Rehabilitation*, 32(2), 101-107.

(14) Gernsbacher, Morton Ann, Michelle Dawson, and H. Hill Goldsmith (2005). "Three Reasons Not to Believe in an Autism Epidemic." *Current Directions in Psychological Science*, 14(2), 55-58.

(15) Granpeesheh, Doreen, Jonathan Tarbox, Adel C. Najdowski, and Julie Kornack (2014). *Evidence-Based Treatment for Children with Autism: The CARD Model*, Academic Press.

(16) Hennessey, Craig, Boma Noureddin, and Peter Lawrence (2006). "A Single Camera Eye-Gaze Tracking System with Free Head Motion." *Proceedings of the 2006 Symposium on Eye Tracking Research & Applications (ETRA)*, San Diego, Calif., March 2006, pp. 87-94.

(17) Horn, B. K. P., and B. G. Schunck (1981). "Determining Optical Flow." *Artificial Intelligence*, 17, 185-203.

(18) Hwang, B., and C. Hughes (2000). "The Effects of Social Interactive Training on Early Social Communicative Skills of Children with Autism." *Journal of Autism and Developmental Disorders*, 30, 331-343.

(19) Ingersoll, Brooke (2008). "The Social Role of Imitation in Autism: Implications for the Treatment of Imitation Deficits." *Infants & Young Children*, 21(2), 107-119.

(20) Dautenhahn, Kerstin, Chrystopher L. Nehaniv, Michael L. Walters, Ben Robins, Hatice Kose-Bagci, N. Assif Mirza, and Mike Blow (2009). "KASPAR—A Minimally Expressive Humanoid Robot for Human-Robot Interaction Research." *Applied Bionics and Biomechanics*, 6(3-4), 369-397.

(21) Lu, Feng, Takahiro Okabe, Yusuke Sugano, and Yoichi Sato (2011). "A Head Pose-free Approach for Appearance-based Gaze Estimation." *The 22nd British Machine Vision Conference*, August 2011, Dundee, Scotland, UK.

(22) Lucas, B. D., and T. Kanade (1981). "An iterative image registration technique with an application to stereo vision." *Proceedings of the DARPA Image Understanding Workshop*, April 1981, pp. 121-130.

(23) Milborrow, Stephen, and Fred Nicolls (2008). "Locating Facial Features with an Extended Active Shape Model." *Proceedings of the European Conference on Computer Vision (ECCV)*, October 2008, Marseille, France, pp. 504-513.

(24) Moore M., and S. Calvert (2000). "Brief Report: Vocabulary Acquisition for Children with Autism: Teacher or Computer Instruction." *Journal of Autism and Developmental Disorders*, 30(4), 359-62.

(25) Morimoto, Carlos H., Marcio R. M. Mimica (2005). "Eye Gaze Tracking Techniques for Interactive Applications." *Computer Vision and Image Understanding*, 98(1), 4-24.

(26) Preston, D., and M. Carter (2009). *Journal of Autism and Developmental Disorders*, "A Review of the Efficacy of the Picture Exchange Communication System Intervention." *Journal of Autism and Developmental Disorders*, 39(10), 1471-1486.

(27) Scassellati, Brian, Henny Admoni, and Maja Matarić (2012). "Robots for Use in Autism Research." *Annual Review of Biomedical Engineering*, 14, 275-294. First published online as a Review in Advance on May 9, 2012.

(28) Scharstein, Daniel, and Richard Szeliski (2002). "A Taxonomy and Evaluation of Dense Two-Frame Stereo Correspondence Algorithms." *International Journal of Computer Vision*, 47(1-3), 7-42.

(29) Steege, M. W., F. C. Mace, L. Perry, and H. Longenecker (2007). "Applied Behavior Analysis: Beyond Discrete Trial Teaching." *Psychology in the Schools*, 44(1), 91-99.

(30) Tapus, Adriana, Andreea Peca, Aly Amir, Cristina Pop, Lavinia Jisa, Sebastian Pintea, Alina Rusu, and Daniel David (2012). "Children with Autism Social Engagement in Interaction with Nao, an Imitative Robot—A Series of Single Case Experiments." *Interaction Studies*, 13(3), 315-347.

(31) Tchaconas, Alexis, and Andrew Adesman (2013). "Autism Spectrum Disorders: A Pediatric Overview and Update." *Current Opinion in Pediatrics*, 25(1), 130-143.

(32) Tiegerman, E., and L. H. Primavera (1984). "Imitating the Autistic Child: Facilitating Communicative Gaze Behavior." *Journal of Autism and Developmental Disorders*, 14, 27-38.

(33) Viola, Paul, and Michael Jones (2001). "Robust Real-time Object Detection." *International Journal of Computer Vision*, 57(2).

(34) Williams C., B. Wright, G. Callaghan, and B. Coughlan (2002). "Do Children with Autism Learn to Read More Readily by Computer Assisted Instruction or Traditional Book Methods? A Pilot Study." *Autism*, 6(1), 71-91.

(35) Zafeiriou, Stefanos, Cha Zhang, and Zhengyou Zhang (2015). "A Survey on Face Detection in the Wild: Past, Present and Future." *Computer Vision and Image Understanding*, 138, 1-24.

(36) Zhang, Cha, and Zhengyou Zhang (2014). "Improving Multiview Face Detection with Multi-Task Deep Convolutional Neural Networks." *Proceedings of the IEEE Winter Conference on Applications of Computer Vision*, Steamboat Springs, Colo., March 2014, pp. 1036-1041.

The following are referred to in the included quotation from Carbone et al, 2013:

(37) Arnold, A., R. J. Semple, I. Beale, and C. M. Fletcher-Flinn (2000). "Eye Contact in Children's Social Interactions: What is Normal Behavior?" *Journal of Intellectual & Developmental Disability*, 25, 207-216.

(38) Baron-Cohen, S., J. Allen, and C. Gillberg (1992). "Can Autism Be Detected at 18 Months? The Needle, the Haystack, and the CHAT." *British Journal of Psychiatry*, 161, 839-843.

(39) Greer, D. R., and D. E. Ross (2007). *Verbal Behavior Analysis*, Pearson Education, New York, N.Y.

(40) Kleinke, C. L. (1986). "Gaze and Eye Contact: A Research Review." *Psychological Bulletin*, 100(1), 78-100.

(41) Lee, K., M. Eskritt, L. A. Symons, and D. Muir (1998). "Children's Use of Triadic Eye Gaze Information for 'Mind Reading'." *Developmental Psychology*, 34(3), 525-539.

(42) Leekam, S., S. Baron-Cohen, D. Perrett, M. Milders, and S. Brown (1997). "Eye-Direction Detection: A Dissociation Between Geometric and Joint Attention Skills in Autism." *British Journal of Developmental Psychology*, 15, 77-95.

(43) Lovaas, O. I. (1977). *The Autistic Child: Language Development through Behavior Modification*, Irvington, New York, N.Y., 1977.

(44) Mirenda, P. L., A. M. Donnellan, and D. E. Yoder (1983). "Gaze Behavior: A New Look at an Old Problem." *Journal of Autism and Developmental Disorders*, 13, 397-409.

(45) Podrouzek, W., and D. Furrow (1988). "Preschoolers' Use of Eye Contact while Speaking: The Influence of Sex, Age, and Conversational Partner." *Journal of Psycholinguistic Research*, 17, 89-98.

(46) Stem, D. (1985). *The Interpersonal World of the Infant*, Basic Books, New York, N.Y., 1985.

(47) Wimpory, D. C., R. P. Hobson, M. G. Williams, and S. Nash (2000). "Are Infants with Autism Socially Engaged? A Study of Recent Retrospective Parental Reports." *Journal of Autism and Developmental Disorders*, 30, 525-536.

(48) Woods, J. J., and A. M. Wetherby (2003). "Early Identification of and Intervention for Infants and Toddlers Who are at Risk for Autism Spectrum Disorder." *Language, Speech, and Hearing Services in Schools*, 34, 180-193.

What is claimed:

1. A therapy method for encouraging a patient diagnosed with autism, an autism spectrum disorder, and/or a neurodevelopment disorder to make eye contact with other individuals, said therapy method comprising:
   treating the patient by placing a robot in a field of view of the patient such that the robot can interact with the patient thereby creating intrinsic motivation in the patient to make eye contact with the other individuals after a therapy session has ended, the robot comprising:
   prominently featured animatronic eyes on a front side thereof;
   a video camera;
   a processor configured to:
      process data from the video camera to determine a gaze direction of the patient during the therapy session; and
      select a gaze direction for the animatronic eyes based on the determined gaze direction of the patient; and
   an actuator that allows the interaction with the patient by controlling the animatronic eyes based on the selected gaze direction for the animatronic eyes; and
   refraining from providing the patient with a positive reinforcement for gazing at the animatronic eyes during the therapy session;
   wherein movement of the animatronic eyes constitutes the only electronically actuated movement of the robot.

2. The therapy method of claim 1, wherein the robot is in the form of a rectangular box or of a toy dog.

3. The therapy method of claim 1, wherein the gaze direction for the animatronic eyes is selected based on a score of possible gaze directions relating to an assertiveness of each of the possible gaze directions.

4. The therapy method of claim 1, wherein the gaze direction for the animatronic eyes is selected based on a ranking of possible gaze directions relating to an assertiveness of each of the possible gaze directions.

5. The therapy method of claim 1, wherein the gaze direction for the animatronic eyes is selected using a process comprising:
   scoring possible gaze directions based on assertiveness;
   excluding some of said possible gaze directions from consideration based on the scoring; and
   choosing randomly amongst the remaining possible gaze directions.

6. The therapy method of claim 1, wherein the gaze direction for the animatronic eyes is selected using a process comprising:
   scoring possible gaze directions based on assertiveness;
   ranking possible gaze directions based on the scoring;
   excluding some of said possible gaze directions from consideration based on the ranking; and
   choosing randomly amongst the remaining possible gaze directions.

7. The therapy method of claim 1, wherein the robot serves to evoke a concept of eye contact.

8. The therapy method of claim 1, wherein the video camera is operative to capture images using infrared radiation or using radiation with wavelengths shorter than radiation that is typically visible to humans.

9. The therapy method of claim 1, wherein said processor is configured to process data from the video camera to determine whether or not the patient is looking at the video camera and/or looking at the animatronic eyes and/or looking at the robot.

10. The therapy method of claim 1, further comprising refraining from providing the patient with a positive reinforcement for making eye contact with people during the therapy session.

11. The therapy method of claim 1, further comprising refraining from providing the patient with a positive reinforcement for making eye contact with said other individuals after the therapy session has ended.

* * * * *